US012800583B2

(12) United States Patent
Kuhn et al.

(10) Patent No.: US 12,800,583 B2
(45) Date of Patent: Nov. 17, 2026

(54) BACTERIAL BIOMARKER FOR RHEUMATOID ARTHRITIS AND RELATED MATERIALS AND METHODS

(71) Applicant: THE REGENTS OF THE UNIVERSITY OF COLORADO, Denver, CO (US)

(72) Inventors: Kristine Kuhn, Denver, CO (US); V. Michael Holers, Denver, CO (US); Kevin Deane, Denver, CO (US); Kristen Demoruelle, Golden, CO (US); Jill Norris, Denver, CO (US); Meagan Chriswell, Aurora, CO (US); William Robinson, Palo Alto, CA (US)

(73) Assignees: The Regents of the University of Colorado, a body corporate, Denver, CO (US); The Board of Trustees of the Leland Stanford Junior University, Stanford, CA (US)

( * ) Notice: Subject to any disclaimer, the term of this patent is extended or adjusted under 35 U.S.C. 154(b) by 597 days.

(21) Appl. No.: 18/251,915

(22) PCT Filed: Nov. 8, 2021

(86) PCT No.: PCT/US2021/072293

§ 371 (c)(1),
(2) Date: May 5, 2023

(87) PCT Pub. No.: WO2022/099317

PCT Pub. Date: May 12, 2022

(65) Prior Publication Data

US 2024/0011986 A1 Jan. 11, 2024

Related U.S. Application Data

(60) Provisional application No. 63/110,753, filed on Nov. 6, 2020.

(51) Int. Cl.
*G01N 33/569* (2006.01)
*A61K 39/02* (2006.01)
(Continued)

(52) U.S. Cl.
CPC .... *G01N 33/56911* (2013.01); *A61K 39/0208* (2013.01); *A61K 39/40* (2013.01);
(Continued)

(58) Field of Classification Search
CPC ......... G01N 33/56911; G01N 2469/20; G01N 2800/102; A61K 39/0008; A61K 38/1774;
(Continued)

(56) References Cited

U.S. PATENT DOCUMENTS

2013/0078237 A1 3/2013 Delaney et al.
2013/0216547 A1 8/2013 Morton et al.
2022/0160712 A1* 5/2022 Turnbaugh ............. C12Q 1/689

FOREIGN PATENT DOCUMENTS

WO WO-2006119115 A2 * 11/2006 ................ A61P 7/00

OTHER PUBLICATIONS

Ahuja et al. "Structural Analysis of Bacterial ABC Transporter Inhibition by an Antibody Fragment," Structure, Apr. 2017, vol. 23, pp. 713-723.

(Continued)

*Primary Examiner* — Jana A Hines
(74) *Attorney, Agent, or Firm* — Sheridan Ross P.C.

(57) ABSTRACT

Therapeutic and prophylactic therapies for rheumatoid arthritis are provided, as are related pharmaceutical compositions. Methods provide for the early detection of subjects at risk of developing rheumatoid arthritis, thus allowing for early intervention, and include methods of sample preparation.

3 Claims, 25 Drawing Sheets

Specification includes a Sequence Listing.

(51) Int. Cl.
*A61K 39/40* (2006.01)
*C12Q 1/689* (2018.01)

(52) U.S. Cl.
CPC ........ *C12Q 1/689* (2013.01); *C12Q 2600/112* (2013.01); *C12Q 2600/156* (2013.01); *G01N 2469/20* (2013.01); *G01N 2800/102* (2013.01)

(58) Field of Classification Search
CPC ............ A61K 38/2006; A61K 39/0208; A61K 39/40; A61K 45/06; A61K 2039/58; C12Q 1/689; C12Q 2600/112; C12Q 2600/156
See application file for complete search history.

(56) References Cited

OTHER PUBLICATIONS

Chriswell et al. "Clonal IgA and IgG autoantibodies from individuals at risk for rheumatoid arthritis identify and arthritogenic strain of Subdoligranulum," Science Translational Medicine, Oct. 2022, vol. 14, No. 668article eabn5166, 16 pages.
UniProtKB Accession No. R5Y4K6_9FIRM, Amino acid ABC transporter substrate-binding protein PAAT family (TC 3.A.1.3.-), Jul. 24, 2013, 4 pages [retrieved online from: www.uniprot.org/uniprotkb/R5Y4K6/entry].
International Search Report and Written Opinion for International (PCT) Patent Application No. PCT/US21/72293, dated Mar. 10, 2022 13 pages.
Holers et al. "Rheumatoid arthritis and the mucosal origins hypothesis: protection turns to destruction," Nature Reviews Rheumatology, Sep. 2018, vol. 14, No. 9, pp. 542-557.
Jubair et al. "Modulation of Inflammatory Arthritis in Mice by Gut Microbiota Through Mucosal Inflammation and Autoantibody Generation," Arthritis & Rheumatology, 2018, vol. 70, No. 8, pp. 1220-1233.
Kinslow et al. "Elevated IgA Plasmablast Levels in Subjects at Risk of Developing Rheumatoid Arthritis," Arthritis & Rheumatology, Oct. 2016, vol. 68, No. 10, pp. 2372-2383.
Mikuls et al. "Antibody responses to Porphyromonas gingivalis (P. gingivalis) in subjects with rheumatoid arthritis and periodontitis," International Immunopharmacology, Jan. 2009, vol. 9, No. 1, pp. 38-42.
Partial Supplementary Search Report for European Patent Application No. 21890351.8, dated Dec. 20, 2024 14 pages.
International Preliminary Report on Patentability for International (PCT) Patent Application No. PCT/US2021/072293, dated May 19, 2023, 9 pages.

* cited by examiner

| Autoantigen | Isolate 7 Mean ± SD | Isolate 1 Mean ± SD | *P. copri* Mean ± SD | Sterile Media Mean ± SD | p-value |
|---|---|---|---|---|---|
| Fibromodulin 345-364 | 2.03 ± 0.97 | 0.72 ± 0.14 | 1.53 ± 0.49 | 1.14 ± 0.54 | 0.004 |
| HCgp39 7-22 | 1.57 ± 0.46 | 0.83 ± 0.24 | 0.92 ± 0.40 | 1.06 ± 0.51 | 0.01 |
| hFibA 211-230 | 1.72 ± 0.92 | 0.56 ± 0.27 | 1.11 ± 0.33 | 1.22 ± 0.29 | 0.003 |
| hFibA 616-635 | 1.18 ± 0.47 | 0.58 ± 0.46 | 0.42 ± 0.29 | 1.22 ± 0.40 | 0.002 |
| Tenascin-C 122-141 cit2 | 2.29 ± 1.53 | 0.78 ± 0.20 | 0.78 ± 0.47 | 0.86 ± 0.41 | 0.001 |
| a-enolase 122-141 cit | 1.24 ± 0.72 | 0.50 ± 0.15 | 0.56 ± 0.36 | 0.72 ± 0.33 | 0.02 |
| Fibromodulin 103-122 | 1.76 ± 0.93 | 0.64 ± 0.37 | 0.92 ± 0.58 | 1.00 ± 0.35 | 0.01 |
| H2A 79-98 | 2.51 ± 1.71 | 0.97 ± 0.22 | 1.22 ± 0.39 | 1.72 ± 0.50 | 0.01 |
| hFibA 246-260 | 1.68 ± 0.89 | 0.86 ± 0.39 | 0.89 ± 0.29 | 0.69 ± 0.25 | 0.01 |
| cH3 | 1.17 ± 0.55 | 0.58 ± 0.25 | 0.61 ± 0.27 | 0.97 ± 0.37 | 0.047 |

BACTERIAL BIOMARKER FOR RHEUMATOID ARTHRITIS AND RELATED MATERIALS AND METHODS

STATEMENT REGARDING FEDERALLY SPONSORED RESEARCH

This invention was made with government support under Grant No. U01AI101981 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 5, 2021, is named 517709.45_PCT-_SL.txt and is 6,741,597 bytes in size.

BACKGROUND

Rheumatoid arthritis (RA) is a progressive, systemic autoimmune disease characterized by chronic inflammation of multiple joints with associated symptoms such as fatigue. The inflammation causes joint pain, stiffness, and swelling resulting in loss of joint function due to destruction of bone and cartilage. RA often leads to progressive disability. Patients with RA also have an increased likelihood of developing other systemic complications such as osteoporosis, anemia, cardiovascular disease, and disorders affecting the lungs and skin. The disease shortens the average life expectancy of affected patients by three to seven years. About 0.5-1% of the US adult population is affected by RA, and given the average age of onset is approximately 50, the number of affected individuals is expected to rise. Despite declining rates of disability attributed to RA, about 30% of patients do not achieve a minimally acceptable symptom state.

Early treatment of RA is associated with decreased joint damage and disability. In addition, studies performed in individuals considered to have pre-RA defined as clinical risk for RA but not yet classifiable disease have demonstrated promising results for RA prevention. However, identification of individuals at risk for developing RA is a challenging and inexact process, and which therapeutic approaches to utilize in individuals who do not yet have arthritis is an emerging area of investigation.

Despite advances in therapy for patients with clinically active RA, significant limitations in efficacy and safety remain. New methods are needed for identifying which therapeutic approach to use in an individual, as is an increased number of therapeutic targets and drugs for RA.

SUMMARY

In a first example ("Example 1"), provided herein is a composition including one or more therapeutic agents directed to *Subdoligranulum didolesgii* strain D8.

In another example ("Example 2"), further to Example 1, the one or more therapeutic agents comprise at least one immunotherapeutic agent.

In another example ("Example 3"), further to Example 2, the at least one immunotherapeutic agent is selected from: an antibody against an antigen of *Subdoligranulum didolesgii* strain D8; an antibody fragment against an antigen of *Subdoligranulum didolesgii* strain D8; a vaccine against *Subdoligranulum didolesgii* strain D8; or any combination thereof.

In another example ("Example 4"), further to Example 3, the antibody against an antigen of *Subdoligranulum didolesgii* strain D8 or the antibody fragment against an antigen of comprises a variable region selected from a variable region of: antibody MH1 ($V_H$=SEQ ID NO: 3; $V_L$=SEQ ID NO: 4); MH3 ($V_H$=SEQ ID NO: 7; $V_L$=SEQ ID NO: 8); MH4 ($V_H$=SEQ ID NO: 9; $V_L$=SEQ ID NO: 10); MH5 ($V_H$=SEQ ID NO: 11; $V_L$=SEQ ID NO: 12); MH6 ($V_H$=SEQ ID NO: 13; $V_L$=SEQ ID NO: 14); MH11 ($V_H$=SEQ ID NO: 23; $V_L$=SEQ ID NO: 24); MH12 ($V_H$=SEQ ID NO: 25; $V_L$=SEQ ID NO: 26); MH14 ($V_H$=SEQ ID NO: 29; $V_L$=SEQ ID NO: 30); MH15 ($V_H$=SEQ ID NO: 31; $V_L$=SEQ ID NO: 32); MH16 ($V_H$=SEQ ID NO: 33; $V_L$=SEQ ID NO: 34); MH17 ($V_H$=SEQ ID NO: 35; $V_L$=SEQ ID NO: 36); MH18 ($V_H$=SEQ ID NO: 37; $V_L$=SEQ ID NO: 38); MH20 ($V_H$=SEQ ID NO: 41; $V_L$=SEQ ID NO: 42); MH21 ($V_H$=SEQ ID NO: 43; $V_L$=SEQ ID NO: 44); MH22 ($V_H$=SEQ ID NO: 45; $V_L$=SEQ ID NO: 46); MH23 ($V_H$=SEQ ID NO: 47; $V_L$=SEQ ID NO: 48); MH24 ($V_H$=SEQ ID NO: 49; $V_L$=SEQ ID NO: 50); MH25 ($V_H$=SEQ ID NO: 51; $V_L$=SEQ ID NO: 52); MH27 ($V_H$=SEQ ID NO: 55; $V_L$=SEQ ID NO: 56); MH28 ($V_H$=SEQ ID NO: 57; $V_L$=SEQ ID NO: 58); MH29 ($V_H$=SEQ ID NO: 59; $V_L$=SEQ ID NO: 60); MH30 ($V_H$=SEQ ID NO: 61; $V_L$=SEQ ID NO: 62); MH31 ($V_H$=SEQ ID NO: 63; $V_L$=SEQ ID NO: 64); MH32 ($V_H$=SEQ ID NO: 65; $V_L$=SEQ ID NO: 66); MH33 ($V_H$=SEQ ID NO: 67; $V_L$=SEQ ID NO: 68); MH34 ($V_H$=SEQ ID NO: 69; $V_L$=SEQ ID NO: 70); MH35 ($V_H$=SEQ ID NO: 71; $V_L$=SEQ ID NO: 72); MH38 ($V_H$=SEQ ID NO: 77; $V_L$=SEQ ID NO: 78); MH39 ($V_H$=SEQ ID NO: 79; $V_L$=SEQ ID NO: 80); MH40 ($V_H$=SEQ ID NO: 81; $V_L$=SEQ ID NO: 82); MH42 ($V_H$=SEQ ID NO: 85; $V_L$=SEQ ID NO: 86); MH45 ($V_H$=SEQ ID NO: 91; $V_L$=SEQ ID NO: 92); MH46 ($V_H$=SEQ ID NO: 93; $V_L$=SEQ ID NO: 94); MH48 ($V_H$=SEQ ID NO: 97; $V_L$=SEQ ID NO: 98), MH49 ($V_H$=SEQ ID NO: 99; $V_L$=SEQ ID NO: 100); MH50 ($V_H$=SEQ ID NO: 101; $V_L$=SEQ ID NO: 102); MH51 ($V_H$=SEQ ID NO: 103; $V_L$=SEQ ID NO: 104); MH55 ($V_H$=SEQ ID NO: 111; $V_L$=SEQ ID NO: 112); MH56 ($V_H$=SEQ ID NO: 113; $V_L$=SEQ ID NO: 114); MH57 ($V_H$=SEQ ID NO: 115; $V_L$=SEQ ID NO: 116); MH58 ($V_H$=SEQ ID NO: 117; $V_L$=SEQ ID NO: 118); MH59 ($V_H$=SEQ ID NO: 119; $V_L$=SEQ ID NO: 120); MH60 ($V_H$=SEQ ID NO: 121; $V_L$=SEQ ID NO: 122); MH62 ($V_H$=SEQ ID NO: 125; $V_L$=SEQ ID NO: 126); MH63 ($V_H$=SEQ ID NO: 127; $V_L$=SEQ ID NO: 128); MH64 ($V_H$=SEQ ID NO: 129; $V_L$=SEQ ID NO: 130); MH65 ($V_H$=SEQ ID NO: 131; $V_L$=SEQ ID NO: 132); MH66 ($V_H$=SEQ ID NO: 133; $V_L$=SEQ ID NO: 134); MH67 ($V_H$=SEQ ID NO: 135; $V_L$=SEQ ID NO: 136); MH68 ($V_H$=SEQ ID NO: 137; $V_L$=SEQ ID NO: 138); MH73 ($V_H$=SEQ ID NO: 147; $V_L$=SEQ ID NO: 148); MH74 ($V_H$=SEQ ID NO: 149; $V_L$=SEQ ID NO: 150) MH75 ($V_H$=SEQ ID NO: 151; $V_L$=SEQ ID NO: 152) MH76 ($V_H$=SEQ ID NO: 153; $V_L$=SEQ ID NO: 154); MH80 ($V_H$=SEQ ID NO: 161; $V_L$=SEQ ID NO: 162); MH82 ($V_H$=SEQ ID NO: 165; $V_L$=SEQ ID NO: 166); MH83 ($V_H$=SEQ ID NO: 187; $V_L$=SEQ ID NO: 188); and MH91 ($V_H$=SEQ ID NO: 183; $V_L$=SEQ ID NO: 184).

In another example ("Example 5"), further to Example 3, the antibody against an antigen of *Subdoligranulum didol-*

*esgii* strain D8 or the antibody fragment against an antigen of comprises a variable region selected from a variable region of: antibody MH4 ($V_H$=SEQ ID NO: 9; $V_L$=SEQ ID NO: 10); MH28 ($V_H$=SEQ ID NO: 57; $V_L$=SEQ ID NO: 58); MH58 ($V_H$=SEQ ID NO: 117; $V_L$=SEQ ID NO: 118); and MH91 ($V_H$=SEQ ID NO: 183; $V_L$=SEQ ID NO: 184).

In another example ("Example 6"), further to Example 3, the vaccine against *Subdoligranulum didolesgii* strain D8 comprises: heat-inactivated *Subdoligranulum didolesgii* strain D8; an antigen polypeptide from *Subdoligranulum didolesgii* strain D8; a nucleic acid encoding an antigen polypeptide from *Subdoligranulum didolesgii* strain D8; or any combination thereof.

In another example ("Example 7"), further to Example 1, the one or more therapeutic agents comprise an antibiotic effective against *Subdoligranulum didolesgii* strain D8.

In another example ("Example 8"), further to Example 1, the one or more therapeutic agents comprise a *Subdoligranulum didolesgii* strain D8 indole inhibitor.

In another example ("Example 9"), further to Example 8, the *Subdoligranulum didolesgii* strain D8 indole inhibitor is selected from: a protein; a peptide; an antibody; a peptidomimetic; a ribozyme; a small molecule; a vector; an antisense nucleic acid; and a CRISPR-based inhibitor.

In another example ("Example 10"), provided herein is a method that includes: reducing a population of *Subdoligranulum didolesgii* strain D8 in the subject; eliminating a population of *Subdoligranulum didolesgii* strain D8 in the subject; inhibiting an indole-containing compound produced by a population of *Subdoligranulum didolesgii* strain D8 in the subject; inhibiting an indole-related pathway in a population of *Subdoligranulum didolesgii* strain D8; inhibiting or preventing an immune response by the subject to *Subdoligranulum didolesgii* strain D8; eliciting a protective immune response in the subject against *Subdoligranulum didolesgii* strain D8; or any combination thereof.

In another example ("Example 11"), further to Example 10, the method includes administering to the subject an effective amount of a composition of any one of Examples 1-9.

In another example ("Example 12"), further to Example 10, the method includes detecting the presence of *Subdoligranulum didolesgii* strain D8 or one or more antibodies against *Subdoligranulum didolesgii* strain D8 in the subject.

In another example ("Example 13"), further to Example 12, the presence of *Subdoligranulum didolesgii* strain D8 is detected by PCR analysis or whole genome sequencing.

In another example ("Example 14"), further to Example 12, the presence of *Subdoligranulum didolesgii* strain D8 is detected by identifying bacteria comprising a genome represented by SEQ ID NO: 2.

In another example ("Example 15"), further to Example 12, the method includes increasing relative abundance of bacteria from Lachnospiraceae, Ruminococcaceae, or both Lachnospiraceae and Ruminococcaceae in a fraction of a sample from the subject.

In another example ("Example 16"), further to Example 15, the sample is a fecal sample, rectal swab, or an intestinal tissue biopsy.

In another example ("Example 17"), further to Example 15 or Example 16, increasing the relative abundance of the bacteria comprises contacting the sample from the subject with one or more monoclonal antibodies or one or more antibody fragments, the one or more monoclonal antibodies or one or more antibody fragments including a variable region selected from: antibody MH1 ($V_H$=SEQ ID NO: 3; $V_L$=SEQ ID NO: 4); MH3 ($V_H$=SEQ ID NO: 7; $V_L$=SEQ ID NO: 8); MH4 ($V_H$=SEQ ID NO: 9; $V_L$=SEQ ID NO: 10); MH5 ($V_H$=SEQ ID NO: 11; $V_L$=SEQ ID NO: 12); MH6 ($V_H$=SEQ ID NO: 13; $V_L$=SEQ ID NO: 14); MH11 ($V_H$=SEQ ID NO: 23; $V_L$=SEQ ID NO: 24); MH12 ($V_H$=SEQ ID NO: 25; $V_L$=SEQ ID NO: 26); MH14 ($V_H$=SEQ ID NO: 29; $V_L$=SEQ ID NO: 30); MH15 ($V_H$=SEQ ID NO: 31; $V_L$=SEQ ID NO: 32); MH16 ($V_H$=SEQ ID NO: 33; $V_L$=SEQ ID NO: 34); MH17 ($V_H$=SEQ ID NO: 35; $V_L$=SEQ ID NO: 36); MH18 ($V_H$=SEQ ID NO: 37; $V_L$=SEQ ID NO: 38); MH20 ($V_H$=SEQ ID NO: 41; $V_L$=SEQ ID NO: 42); MH21 ($V_H$=SEQ ID NO: 43; $V_L$=SEQ ID NO: 44); MH22 ($V_H$=SEQ ID NO: 45; $V_L$=SEQ ID NO: 46); MH23 ($V_H$=SEQ ID NO: 47; $V_L$=SEQ ID NO: 48); MH24 ($V_H$=SEQ ID NO: 49; $V_L$=SEQ ID NO: 50); MH25 ($V_H$=SEQ ID NO: 51; $V_L$=SEQ ID NO: 52); MH27 ($V_H$=SEQ ID NO: 55; $V_L$=SEQ ID NO: 56); MH28 ($V_H$=SEQ ID NO: 57; $V_L$=SEQ ID NO: 58); MH29 ($V_H$=SEQ ID NO: 59; $V_L$=SEQ ID NO: 60); MH30 ($V_H$=SEQ ID NO: 61; $V_L$=SEQ ID NO: 62); MH31 ($V_H$=SEQ ID NO: 63; $V_L$=SEQ ID NO: 64); MH32 ($V_H$=SEQ ID NO: 65; $V_L$=SEQ ID NO: 66); MH33 ($V_H$=SEQ ID NO: 67; $V_L$=SEQ ID NO: 68); MH34 ($V_H$=SEQ ID NO: 69; $V_L$=SEQ ID NO: 70); MH35 ($V_H$=SEQ ID NO: 71; $V_L$=SEQ ID NO: 72); MH38 ($V_H$=SEQ ID NO: 77; $V_L$=SEQ ID NO: 78); MH39 ($V_H$=SEQ ID NO: 79; $V_L$=SEQ ID NO: 80); MH40 ($V_H$=SEQ ID NO: 81; $V_L$=SEQ ID NO: 82); MH42 ($V_H$=SEQ ID NO: 85; $V_L$=SEQ ID NO: 86); MH45 ($V_H$=SEQ ID NO: 91; $V_L$=SEQ ID NO: 92); MH46 ($V_H$=SEQ ID NO: 93; $V_L$=SEQ ID NO: 94); MH48 ($V_H$=SEQ ID NO: 97; $V_L$=SEQ ID NO: 98), MH49 ($V_H$=SEQ ID NO: 99; $V_L$=SEQ ID NO: 100); MH50 ($V_H$=SEQ ID NO: 101; $V_L$=SEQ ID NO: 102); MH51 ($V_H$=SEQ ID NO: 103; $V_L$=SEQ ID NO: 104); MH55 ($V_H$=SEQ ID NO: 111; $V_L$=SEQ ID NO: 112); MH56 ($V_H$=SEQ ID NO: 113; $V_L$=SEQ ID NO: 114); MH57 ($V_H$=SEQ ID NO: 115; $V_L$=SEQ ID NO: 116); MH58 ($V_H$=SEQ ID NO: 117; $V_L$=SEQ ID NO: 118); MH59 ($V_H$=SEQ ID NO: 119; $V_L$=SEQ ID NO: 120); MH60 ($V_H$=SEQ ID NO: 121; $V_L$=SEQ ID NO: 122); MH62 ($V_H$=SEQ ID NO: 125; $V_L$=SEQ ID NO: 126); MH63 ($V_H$=SEQ ID NO: 127; $V_L$=SEQ ID NO: 128); MH64 ($V_H$=SEQ ID NO: 129; $V_L$=SEQ ID NO: 130); MH65 ($V_H$=SEQ ID NO: 131; $V_L$=SEQ ID NO: 132); MH66 ($V_H$=SEQ ID NO: 133; $V_L$=SEQ ID NO: 134); MH67 ($V_H$=SEQ ID NO: 135; $V_L$=SEQ ID NO: 136); MH68 ($V_H$=SEQ ID NO: 137; $V_L$=SEQ ID NO: 138); MH73 ($V_H$=SEQ ID NO: 147; $V_L$=SEQ ID NO: 148); MH74 ($V_H$=SEQ ID NO: 149; $V_L$=SEQ ID NO: 150) MH75 ($V_H$=SEQ ID NO: 151; $V_L$=SEQ ID NO: 152) MH76 ($V_H$=SEQ ID NO: 153; $V_L$=SEQ ID NO: 154); MH80 ($V_H$=SEQ ID NO: 161; $V_L$=SEQ ID NO: 162); MH82 ($V_H$=SEQ ID NO: 165; $V_L$=SEQ ID NO: 166); MH83 ($V_H$=SEQ ID NO: 187; $V_L$=SEQ ID NO: 188); and MH91 ($V_H$=SEQ ID NO: 183; $V_L$=SEQ ID NO: 184).

In another example ("Example 18"), further to Example 17, the method includes releasing bacteria from the one or more monoclonal antibodies or one or more antibody fragments.

In another example ("Example 19"), further to Example 17 or Example 18, the method includes detecting presence or absence of *Subdoligranulum didolesgii* strain D8 following the contacting step.

In another example ("Example 20"), further to Example 19, detecting the presence or absence of *Subdoligranulum*

*didolesgii* strain D8 includes a polymerase chain reaction (PCR) step or a multiple displacement amplification (MDA) step.

In another example ("Example 21"), further to Example 12, the presence of one or more antibodies against *Subdoligranulum didolesgii* strain D8 is detected by contacting a serum sample or a fecal sample from the subject with isolated *Subdoligranulum didolesgii* strain D8, or one or more isolated antigens thereof, and detecting binding of one or more serum or fecal antibodies to the isolated *Subdoligranulum didolesgii* strain D8 or the one or more isolated antigens thereof.

In another example ("Example 22"), further to any one of Examples 10-21, the method includes administering to the subject one or more compounds selected from: a non-steroidal anti-inflammatory drug; a corticosteroid; a disease-modifying antirheumatic drug; and a biologic response modifier.

In another example ("Example 23"), further to Example 22, a) the non-steroidal anti-inflammatory drug is selected from: ibuprofen; naproxen sodium; celecoxib; diclofenac; fenoprofen; flurbiprofen; indomethacin; ketorolac; mefenamic acid; meloxicam; oxaprozin; piroxicam; and sulindac; the corticosteroid is selected from: prednisone; bethamethasone; and prednisolone; triamcinolone; methylprednisolone; and dexamethasone; b) the disease-modifying antirheumatic drug is selected from: methotrexate; leflunomide; hydroxychloroquine; and sulfasalazine; and c) the biologic response modifier is selected from: abatacept and biosimilars thereof; adalimumab and biosimilars thereof; anakinra and biosimilars thereof; baricitinib; certolizumab and biosimilars thereof; etanercept and biosimilars thereof; golimumab and biosimilars thereof; infliximab and biosimilars thereof; rituximab and biosimilars thereof; sarilumab and biosimilars thereof; tocilizumab and biosimilars thereof; and tofacitinib.

In another example ("Example 24"), provided herein is a method for preparing a sample fraction for detection of *Subdoligranulum didolesgii* strain D8 in a subject, including contacting a sample from the subject selected from a fecal sample, a fecal swab, or an intestinal biopsy with one or more monoclonal antibodies or one or more antibody fragments including a variable region selected from: antibody MH1 ($V_H$=SEQ ID NO: 3; $V_L$=SEQ ID NO: 4); MH3 ($V_H$=SEQ ID NO: 7; $V_L$=SEQ ID NO: 8); MH4 ($V_H$=SEQ ID NO: 9; $V_L$=SEQ ID NO: 10); MH5 ($V_H$=SEQ ID NO: 11; $V_L$=SEQ ID NO: 12); MH6 ($V_H$=SEQ ID NO: 13; $V_L$=SEQ ID NO: 14); MH11 ($V_H$=SEQ ID NO: 23; $V_L$=SEQ ID NO: 24); MH12 ($V_H$=SEQ ID NO: 25; $V_L$=SEQ ID NO: 26); MH14 ($V_H$=SEQ ID NO: 29; $V_L$=SEQ ID NO: 30); MH15 ($V_H$=SEQ ID NO: 31; $V_L$=SEQ ID NO: 32); MH16 ($V_H$=SEQ ID NO: 33; $V_L$=SEQ ID NO: 34); MH17 ($V_H$=SEQ ID NO: 35; $V_L$=SEQ ID NO: 36); MH18 ($V_H$=SEQ ID NO: 37; $V_L$=SEQ ID NO: 38); MH20 ($V_H$=SEQ ID NO: 41; $V_L$=SEQ ID NO: 42); MH21 ($V_H$=SEQ ID NO: 43; $V_L$=SEQ ID NO: 44); MH22 ($V_H$=SEQ ID NO: 45; $V_L$=SEQ ID NO: 46); MH23 ($V_H$=SEQ ID NO: 47; $V_L$=SEQ ID NO: 48); MH24 ($V_H$=SEQ ID NO: 49; $V_L$=SEQ ID NO: 50); MH25 ($V_H$=SEQ ID NO: 51; $V_L$=SEQ ID NO: 52); MH27 ($V_H$=SEQ ID NO: 55; $V_L$=SEQ ID NO: 56); MH28 ($V_H$=SEQ ID NO: 57; $V_L$=SEQ ID NO: 58); MH29 ($V_H$=SEQ ID NO: 59; $V_L$=SEQ ID NO: 60); MH30 ($V_H$=SEQ ID NO: 61; $V_L$=SEQ ID NO: 62); MH31 ($V_H$=SEQ ID NO: 63; $V_L$=SEQ ID NO: 64); MH32 ($V_H$=SEQ ID NO: 65; $V_L$=SEQ ID NO: 66); MH33 ($V_H$=SEQ ID NO: 67; $V_L$=SEQ ID NO: 68); MH34 ($V_H$=SEQ ID NO: 69; $V_L$=SEQ ID NO: 70); MH35 ($V_H$=SEQ ID NO: 71; $V_L$=SEQ ID NO: 72); MH38 ($V_H$=SEQ ID NO: 77; $V_L$=SEQ ID NO: 78); MH39 ($V_H$=SEQ ID NO: 79; $V_L$=SEQ ID NO: 80); MH40 ($V_H$=SEQ ID NO: 81; $V_L$=SEQ ID NO: 82); MH42 ($V_H$=SEQ ID NO: 85; $V_L$=SEQ ID NO: 86); MH45 ($V_H$=SEQ ID NO: 91; $V_L$=SEQ ID NO: 92); MH46 ($V_H$=SEQ ID NO: 93; $V_L$=SEQ ID NO: 94); MH48 ($V_H$=SEQ ID NO: 97; $V_L$=SEQ ID NO: 98), MH49 ($V_H$=SEQ ID NO: 99; $V_L$=SEQ ID NO: 100); MH50 ($V_H$=SEQ ID NO: 101; $V_L$=SEQ ID NO: 102); MH51 ($V_H$=SEQ ID NO: 103; $V_L$=SEQ ID NO: 104); MH55 ($V_H$=SEQ ID NO: 111; $V_L$=SEQ ID NO: 112); MH56 ($V_H$=SEQ ID NO: 113; $V_L$=SEQ ID NO: 114); MH57 ($V_H$=SEQ ID NO: 115; $V_L$=SEQ ID NO: 116); MH58 ($V_H$=SEQ ID NO: 117; $V_L$=SEQ ID NO: 118); MH59 ($V_H$=SEQ ID NO: 119; $V_L$=SEQ ID NO: 120); MH60 ($V_H$=SEQ ID NO: 121; $V_L$=SEQ ID NO: 122); MH62 ($V_H$=SEQ ID NO: 125; $V_L$=SEQ ID NO: 126); MH63 ($V_H$=SEQ ID NO: 127; $V_L$=SEQ ID NO: 128); MH64 ($V_H$=SEQ ID NO: 129; $V_L$=SEQ ID NO: 130); MH65 ($V_H$=SEQ ID NO: 131; $V_L$=SEQ ID NO: 132); MH66 ($V_H$=SEQ ID NO: 133; $V_L$=SEQ ID NO: 134); MH67 ($V_H$=SEQ ID NO: 135; $V_L$=SEQ ID NO: 136); MH68 ($V_H$=SEQ ID NO: 137; $V_L$=SEQ ID NO: 138); MH73 ($V_H$=SEQ ID NO: 147; $V_L$=SEQ ID NO: 148); MH74 ($V_H$=SEQ ID NO: 149; $V_L$=SEQ ID NO: 150) MH75 ($V_H$=SEQ ID NO: 151; $V_L$=SEQ ID NO: 152) MH76 ($V_H$=SEQ ID NO: 153; $V_L$=SEQ ID NO: 154); MH80 ($V_H$=SEQ ID NO: 161; $V_L$=SEQ ID NO: 162); MH82 ($V_H$=SEQ ID NO: 165; $V_L$=SEQ ID NO: 166); MH83 ($V_H$=SEQ ID NO: 187; $V_L$=SEQ ID NO: 188); and MH91 ($V_H$=SEQ ID NO: 183; $V_L$=SEQ ID NO: 184), wherein after contacting the sample with the one or more monoclonal antibodies or the one or more antibody fragments, the resulting fraction comprises an increased relative abundance of bacteria from Lachnospiraceae, Ruminococcaceae, or both Lachnospiraceae and Ruminococcaceae in the sample fraction.

In another example ("Example 25"), further to Example 24, the method includes releasing the bacteria in the sample fraction from the one or more monoclonal antibodies or one or more antibody fragments.

In another example ("Example 26"), further to Example 24 or Example 25, the contacting comprises use of an immunoprecipitation assay.

In another example ("Example 27"), provided herein is a method that includes contacting a serum sample or a fecal sample from a subject with isolated *Subdoligranulum didolesgii* strain D8, or one or more isolated antigens thereof, and detecting binding of one or more antibodies in the serum sample or the fecal sample to the isolated *Subdoligranulum didolesgii* strain D8 or the one or more isolated antigens thereof.

In another example ("Example 28"), provided herein is a method that includes detecting in the subject the presence or absence of *Subdoligranulum didolesgii* strain D8, or detecting in the subject the presence or absence of one or more antibodies against *Subdoligranulum didolesgii* strain D8 or any antigen thereof, wherein detecting the presence of *Subdoligranulum didolesgii* strain D8 or detecting the presence of one or more antibodies against *Subdoligranulum didolesgii* strain D8 or an antigen thereof identifies the subject as being at risk of developing rheumatoid arthritis (RA), as having preclinical RA, or as having RA.

In another example ("Example 29"), further to Example, detecting in the subject the presence or absence of *Subdoligranulum didolesgii* strain D8 includes performing the method of Example 21.

In another example ("Example 30"), further to Example 29, the contacting comprises use of an immunoprecipitation assay.

In another example ("Example 31"), further to any one of Examples 28-30, the presence or absence of *Subdoligranulum didolesgii* strain D8 is detected by PCR analysis or whole genome sequencing.

In another example ("Example 32"), further to Example 29, detecting the presence or absence of one or more antibodies against *Subdoligranulum didolesgii* strain D8 or any antigen thereof comprises contacting a serum sample or a fecal sample from the subject with isolated *Subdoligranulum didolesgii* strain D8, or one or more isolated antigens thereof, and detecting binding of one or more serum antibodies to the isolated *Subdoligranulum didolesgii* strain D8 or the one or more isolated antigens thereof.

In another example ("Example 33"), further to any one of Examples 28-32, the method includes reducing a population of *Subdoligranulum didolesgii* strain D8 in the subject; eliminating a population of *Subdoligranulum didolesgii* strain D8 in the subject; inhibiting an indole-containing compound produced by a population of *Subdoligranulum didolesgii* strain D8 in the subject; inhibiting an indole-related pathway in a population of *Subdoligranulum didolesgii* strain D8; inhibiting or preventing an immune response by the subject to *Subdoligranulum didolesgii* strain D8; eliciting a protective immune response in the subject against *Subdoligranulum didolesgii* strain D8; or any combination thereof.

In another example ("Example 34"), further to Example 33, the method includes administering to the subject an effective amount of a composition of any one of Examples 1-9.

In another example ("Example 35"), further to Example 33 or Example 34, the method includes administering to the subject one or more compounds selected from: a non-steroidal inflammatory drug; a corticosteroid; a disease-modifying antirheumatic drug; and a biologic response modifier.

In another example ("Example 36"), further to Example 35: a) the non-steroidal inflammatory drug is selected from: ibuprofen; naproxen sodium; celecoxib; diclofenac; fenoprofen; flurbiprofen; indomethacin; ketorolac; mefenamic acid; meloxicam; oxaprozin; piroxicam; and sulindac; b) the corticosteroid is selected from: prednisone; bethamethasone; and prednisolone; triamcinolone; methylprednisolone; and dexamethasone; c) the disease-modifying antirheumatic drug is selected from: methotrexate; leflunomide; hydroxychloroquine; and sulfasalazine; and d) the biologic response modifier is selected from: abatacept; adalimumab; anakinra; baricitinib; certolizumab; etanercept; golimumab; infliximab; rituximab; sarilumab; tocilizumab; and tofacitinib.

In a further example ("Example 37"), provided herein is a method of reducing or eliminating a population of *Subdoligranulum didolesgii* strain D8 or a variant of *Subdoligranulum didolesgii* strain D8 in a subject; comprising administering to the subject an effective amount of an antisense nucleic acid or a CRISPR-based inhibitor targeted to a nucleic acid sequence of *Subdoligranulum didolesgii* strain D8 or a variant of *Subdoligranulum didolesgii* strain D8, and/or administering to the subject an effective amount of a composition of any one of Examples 1-9.

In another example ("Example 38"), further to Example 37, the *Subdoligranulum didolesgii* strain D8 comprises SEQ ID NO: 2 or a variant thereof.

In another example ("Example 39"), further to Example 38, the variant comprise at least about 70% identity to SEQ ID NO: 2 and has a least one property selected from: causes local intestinal isolated lymphoid follicles (ILF) formation, stimulates T cell activation, induces development of RA-related autoantibodies, and induces joint swelling.

In another example ("Example 40"), further to Example 37, Example 38, or Example 39, the subject is at risk of (or susceptible to) developing RA, has preclinical RA, has early RA, or has RA.

In another example ("Example 41"), further to Example 37, Example 38, Example 39, or Example 40, the method prevents rheumatoid arthritis in the subject, delays onset of rheumatoid arthritis in the subject, treats rheumatoid arthritis in the subject, or ameliorates at least one symptom of rheumatoid arthritis in the subject.

In another example ("Example 42"), further to Example 37, Example 38, Example 39, Example 40, or Example 41, T the relative abundance of bacteria from Lachnospiraceae, Ruminococcaceae, or both Lachnospiraceae and Ruminococcaceae is decreased in a fraction of a sample from the subject after the administration step.

In another example ("Example 43"), further to Example 442, the sample is a fecal sample, rectal swab, or an intestinal tissue biopsy.

In another example ("Example 44"), further to Example 37, Example 38, Example 39, Example 40, Example 41, Example 42, or Example 43, the method includes administering to the subject one or more compounds selected from: a non-steroidal anti-inflammatory drug; a corticosteroid; a disease-modifying antirheumatic drug; and a biologic response modifier.

In another example ("Example 45"), further to Example 44, a) the non-steroidal anti-inflammatory drug is selected from: ibuprofen; naproxen sodium; celecoxib; diclofenac; fenoprofen; flurbiprofen; indomethacin; ketorolac; mefenamic acid; meloxicam; oxaprozin; piroxicam; and sulindac; the corticosteroid is selected from: prednisone; bethamethasone; and prednisolone; triamcinolone; methylprednisolone; and dexamethasone; b) the disease-modifying antirheumatic drug is selected from: methotrexate; leflunomide; hydroxychloroquine; and sulfasalazine; and c) the biologic response modifier is selected from: abatacept and biosimilars thereof; adalimumab and biosimilars thereof; anakinra and biosimilars thereof; baricitinib; certolizumab and biosimilars thereof; etanercept and biosimilars thereof; golimumab and biosimilars thereof; infliximab and biosimilars thereof; rituximab and biosimilars thereof; sarilumab and biosimilars thereof; tocilizumab and biosimilars thereof; and tofacitinib.

BRIEF DESCRIPTION OF THE DRAWINGS

FIG. 9A depicts data of the presence of FITC-Dextran, to assess intestinal barrier permeability. FITC-Dextran was orally gavaged into mice monocolonized with isolate 1 (n=5), isolate 7 (n=5), *P. copri* (n=6) or sterile media (n=6) 4 hours before euthanasia. At the time of euthanasia, serum was collected and tested for the presence of FITC-Dextran. *=P<0.05.

FIG. 9B depicts intestinal histology data for the mice of the four treatment groups of FIG. 9A. The data are the number and size of isolated lymphoid follicles (ILFs) per colon.

FIG. 9C depicts data for fecal IgA quantity in mice monocolonized with isolate 1 (n=12 gavaged), isolate 7 (n=11 gavaged), *P. copri* (n=6 gavaged) or sterile media (n=12 gavaged). Feces were collected at day 14 after gavage and total IgA concentration was assessed ELISA. *=P<0.05. ****=P<0.0001.

FIG. 9D (MS-5E) depicts data from flow cytometric analysis of Th17 and Treg populations in monocolonized mice. The ratio of Th17/Treg cells is displayed. Mesenteric Lymph Nodes (MLNs) and Peyer's Patches (PPs) were collected from monocolonized mice at 14 days post-gavage (n=7 isolate 7 gavaged, n=7 isolate 1 gavaged, n=7 *P. copri* gavaged, n=8 sterile media gavaged). These tissues were processed and stained for flow cytometric analysis of Th17 and Treg populations. *=P<0.05.

FIG. 10A depicts data for joint swelling. Joint swelling and ankylosis was assessed every seven days subsequently out to 35 days after gavage. (n=5 isotype control dosed, n=4 B cell depleted, n=5 T cell depleted, n=5 neutrophil depleted). FIG. 10B depicts intestinal histology data for the mice. Colonic tissue was collected from isotype control dosed mice as well as T cell and B cell depleted mice at day 35 after bacterial gavage. This tissue was fixed and sectioned, and isolated lymphoid follicles were counted as well as the aggregate size of the ILFs in sum (shown in square microns). FIGS. 10C-10F depict total IgG and IgA in serum and feces from the mice. Serum and feces were collected from the mice at days 14 and 35 post-bacterial gavage. Total IgG and IgA were determined for each of these samples (shown in ng/mL). FIG. 10G depicts data for healthy germ-free DBA/1 mice injected with serium from mice monocolonized with isolate 1, isolate 7, and *P. copri* 35 days after bacterial gavage. Serum was injected IP and the mice were monitored for the development of joint swelling and ankylosis every seven days for 28 days after serum transfer. (n=6 isolate 7 serum transfer, n=6 isolate 1 serum transfer, n=7 *P. copri* serum transfer).

DETAILED DESCRIPTION

Figure 1A:
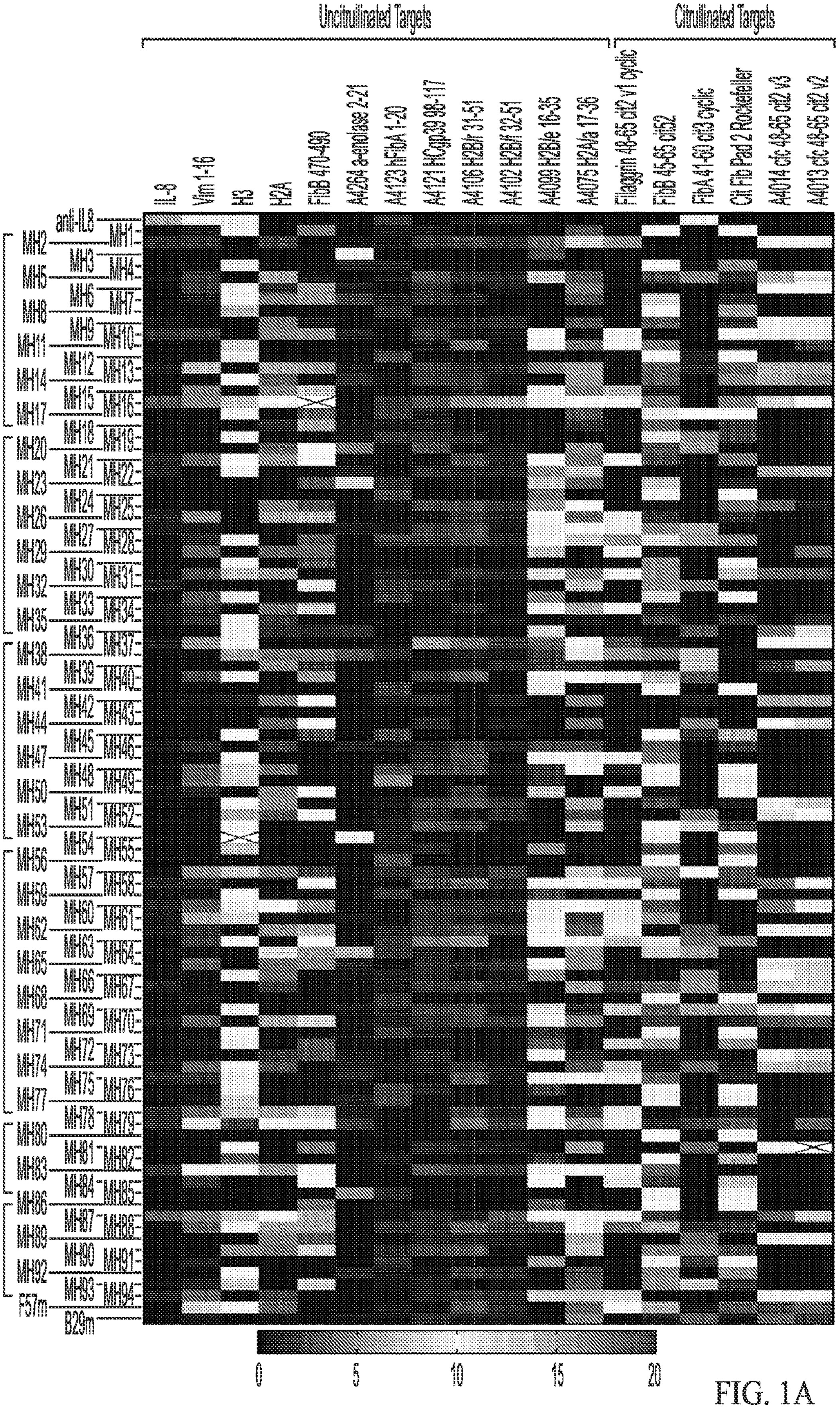
FIG. 1A is a heatmap representing relative reactivity between plasmablast monoclonal antibodies (mAbs) derived from 4 asymptomatic pre-RA subjects (Subject 1: M1-M18; Subject 2 M19-M36; Subject 3: M37-54; and Subject 4: M55-M54 with antigens and 2 early (<1 year of disease) RA patients (Subject 5: M79-M85 and Subject 6L M86-M94) in a synovial antigen array representing a range of citrullinated and non-citrullinated antigens relevant to RA.

In the following sections, various compositions and methods are described in order to detail various embodiments. Practicing the various embodiments does not require the employment of all of the specific details outlined herein, but rather concentrations, times, and other specific details may be modified. In some cases, well known methods or components have not been included in the description.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, and/or (4) to slow the progression of the condition or one or more of the biological manifestations of the condition. The terms "prevent," "preventing," and the like are to be understood to refer to a method of blocking the onset of disease and/or its attendant symptoms. "Prevent" also encompasses delaying or otherwise impeding the onset of a disease and/or its attendant symptoms.

As used herein, "therapeutically effective amount" in reference to an agent means an amount of the agent sufficient to treat the subject's condition but low enough to avoid serious side effects at a reasonable benefit/risk ratio within the scope of sound medical judgment. The safe and effective amount of an agent will vary with the particular agent chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be determined by the skilled artisan.

For any compound, agent, or composition, the therapeutically effective amount can be estimated initially either in cell culture assays or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

A "subject" means any individual having, having symptoms of, or at risk for developing rheumatoid arthritis (RA). A subject may be human or non-human, and may include, for example, animals or species used as "model systems" for research purposes, such as a mouse model. In certain embodiments, the subject is a human patient having RA or at risk of developing RA. As used herein, "at-risk of developing RA" is defined as an individual that is a first-degree relative (FDR) of a patient with RA or an individual with preclinical RA. "Preclinical RA" refers to the presence of positive levels of circulating RA-specific autoantibodies, i.e., serum anti-cyclic citrullinated peptide positive (CCP+) and/or RF positive (RF+). In an embodiment, circulating RA-specific autoantibodies refers to serum anti-CCP3/anti-CCP3.1 positive and/or >2 RF isotypes.

As used herein, "having RA" is defined as an individual diagnosed using American College of Rheumatology (ACR) 1987 and/or ACR European League Against Rheumatism (EULAR) 2010 classification criteria; such criteria include exhibiting clinical symptoms and clinical signs and biomarkers of rheumatoid arthritis. As used herein, "early RA" refers to an individual within one year of RA diagnosis.

As used herein, a "pharmaceutical composition" is a formulation containing a compound or agent in a form suitable for administration to a subject. Compounds and agents disclosed herein each can be formulated individually or in any combination into one or more pharmaceutical compositions. Accordingly, one or more administration routes can be properly elected based on the dosage form of each pharmaceutical composition. Alternatively, a compound or agent disclosed herein and one or more other therapeutic agents described herein can be formulated as one pharmaceutical composition.

Described herein is a novel species and strain of *Subdoligranulum* identified as being sufficient to cause rheumatoid arthritis (RA) or to worsen its disease course and effects on involved tissues. Embodiments of the present disclosure provide methods for identifying subjects at risk of developing RA, having pre-RA, or having RA. Such methods generally include detecting the presence or absence of the disclosed *Subdoligranulum* sp. nov. in the subject, with the presence of the *Subdoligranulum* sp. nov. being linked to a risk of developing RA or indicative of pre-RA or RA in the subject. Also provided are methods for preventing development and/or progression of RA in a subject, or treating RA in a subject. Such methods generally involve administering to a subject in need of treatment one or more therapeutic agents directed to (i.e., capable of reducing the amount or activity) the *Subdoligranulum* sp. nov.

Using multiple independent methods, the inventors have identified a specific bacterial strain in the family Ruminococcus genus *Subdoligranulum* that is targeted by autoantibodies of individuals at risk for RA and those with classified RA. The *Subdoligranulum* sp. nov. is demonstrated to be sufficient to cause the development of arthritis in mice. The strain, designated *Subdoligranulum didolesgii* strain D8, is being maintained in the lab of inventor Kuhn and will be deposited with a depository in accordance with the Budapest Treaty. The instant disclosure will be updated with details of the deposit once available. A genome contig of *S. didolesgii* strain D8 is provided in SEQ ID NO: 2.

With regard to *S. didolesgii* strain D8, the term "polynucleotide" as used in accordance with the present disclosure relates to a polynucleotide comprising a nucleic acid sequence of SEQ ID NO: 2 or a variant of SEQ ID NO: 2. The polynucleotide variants, preferably, comprise a nucleic acid sequence characterized in that the sequence can be derived from SEQ ID NO: 2 by at least one nucleotide substitution, addition and/or deletion. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N. Y. (1989), 6.3.1-6.3.6. A preferred example for stringent hybridization conditions are hybridization conditions in 6×sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer.

The percent identity values are generally calculated over the entire nucleic acid sequence region. In embodiments, the percent identity values are calculated over the entire nucleic acid sequence region. A series of programs based on a variety of algorithms is available to the skilled worker for comparing different sequences.

A mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator "www.ncbi.nlm.nih.gov/BLAST/". BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences having sequence identity to a nucleic acid described herein.

In another embodiment, the percent identity between two nucleotide sequences is determined using the needle program in the EMBOSS software package (*EMBOSS: The European Molecular Biology Open Software Suite*, Rice, P., Longden, I., and Bleasby, A, Trends in Genetics 16(6), 276-277, 2000), using the EDNAFULL scoring matrix and a gap opening penalty of 16, 14, 12, 10, 8, 6, or 4 and a gap extension penalty of 0.5, 1, 2, 3, 4, 5, or 6.

To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See www.ncbi.nlm.nih.gov.

The percent identity between two sequences can be determined using techniques similar to those described above, with or without allowing gaps. In calculating percent identity, typically exact matches are counted.

Variants encompassed by the present disclosure include polynucleotides comprising nucleic acid sequences which are at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3. at least 99.4%, at least 99.5%, at least 99.6%, at least 99.7%, at least 99.75%, at least 99.8%, at least 99.85%, or at least 99.9% identical to SEQ ID NO: 2. Variants encompassed by the present disclosure have up to about 25,000 nucleotide differences (e.g., substitutions, additions and/or deletions) compared to SEQ ID NO: 2 Variants encompassed by the present disclosure have up to 20,000 nucleotide differences compared to SEQ ID NO: 2, up to 10,000, up to 7500, up to 7525, up to 7000, up to 6500, up to 6000, up to 5500, up to 5000, up to 4500, up to 4000, up to 3500, up to 3000, up to 2500, up to 2000, up to 1500, or up to 1000 nucleotide differences compared to SEQ ID NO: 2.

Variants encompassed include *Subdoligranulum didolesgii* strains comprising nucleic acid sequences which are at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3. at least 99.4%, at least 99.5%, at least 99.6%, at least 99.7%, at least 99.75%, at least 99.8%, at least 99.85%, or at least 99.9% identical to SEQ ID NO: 2. Variants encompassed include *Subdoligranulum didolesgii* strains comprising nucleic acid sequences which have up to about 25,000 nucleotide differences compared to SEQ ID NO: 2 Variants encompassed by the present disclosure have up to 20,000 nucleotide differences compared to SEQ ID NO: 2, up to 10,000, up to 7500, up to 7525, up to 7000, up to 6500, up to 6000, up to 5500, up to 5000, up to 4500, up to 4000, up to 3500, up to 3000, up to 2500, up to 2000, up to 1500, or up to 1000 nucleotide differences compared to SEQ ID NO: 2. Variants encompassed by the present disclosure have up to 20,000 nucleotide substitutions compared to SEQ ID NO: 2, up to 10,000, up to 7500, up to 7525, up to 7000, up to 6500, up to 6000, up to 5500, up to 5000, up to 4500, up to 4000, up to 3500, up to 3000, up to 2500, up to 2000, up to 1500, or up to 1000 nucleotide substitutions compared to SEQ ID NO: 2. In certain embodiments, a variant strain comprises at least one target antigen as described herein. In certain embodiments, a variant strain comprises at least one target antigen as described herein. In certain embodiments, a variant strain comprises at least one property selected from causes local intestinal isolated lymphoid follicles (ILF) formation, stimulates T cell activation, induces development of RA-related autoantibodies, and induces joint swelling.

Compositions including one or more therapeutic agents directed to *S. didolesgii* strain D8 or a variant thereof are provided. Agents directed to *S. didolesgii* strain D8 are capable of reducing the amount of the bacteria in a subject and/or are capable of reducing the activity (i.e., mechanism of pathogenicity) of *S. didolesgii* strain D8. The one or more therapeutic agents can be, for example, immunotherapeutic agents, antibiotics, or metabolic inhibitors.

Immunotherapeutic agents directed to *S. didolesgii* strain D8 include antibodies against an antigen of *S. didolesgii* strain D8, antibody fragments against an antigen of *S. didolesgii* strain D8, a vaccine against *S. didolesgii* strain D8, and combinations thereof. Antibodies capable of binding *S. didolesgii* strain D8 are provided, as are vaccines capable of eliciting an immune response against *S. didolesgii* strain D8.

Methods for reducing or eliminating a population of *S. didolesgii* strain D8 in a subject, inhibiting or preventing an immune response by the subject to *S. didolesgii* strain D8, and eliciting a protective immune response in the subject against *S. didolesgii* strain D8 are provided. Such methods include administering to a subject an effective amount of a composition described herein. These methods are useful for preventing RA, delaying onset of RA, treating RA, or ameliorating a symptom or biomarker of RA in a subject in need thereof. In addition to administering an effective amount of a compound described herein, the methods can further include detecting the presence or absence of *S. didolesgii* strain D8 in the subject. The methods can also further include administering to the subject a traditional RA therapeutic, such as non-steroidal inflammatory drugs, corticosteroids, disease-modifying antirheumatic drugs, and biologic response modifiers.

Also provided are methods for preparing a sample fraction that allows for detection of *S. didolesgii* strain D8, or a variant thereof, in a biological sample, as well as methods for detecting *S. didolesgii* strain D8 in a biological sample and for detecting one or more antibodies against *S. didolesgii* strain D8 in a biological sample.

In some embodiments, the presence of *S. didolesgii* strain D8, or a variant thereof, in a subject, or presence of antibodies against *S. didolesgii* strain D8 in subject, identifies the subject as being at risk of developing rheumatoid arthritis, such as having preclinical RA, or as having RA.

Antibodies

Antibodies, and fragments thereof, capable of binding to *S. didolesgii* strain D8 or one or more antigens thereof are provided. In some embodiments, the antibodies or fragments thereof inhibit the activity of *S. didolesgii* strain D8. In other embodiments, the antibodies or fragments thereof induce an immune response against *S. didolesgii* strain D8 in a subject.

Antibodies capable of binding to *S. didolesgii* strain D8 encompass, inter alia, antibodies that bind to an antigen of interest on *S. didolesgii* strain D8, and are able to bind the antigen present on Western blots, in solution in enzyme-linked immunoassays, in fluorescence activated cells sorting (FACS) assays, in magnetic-activated cell sorting (MACS) assays, and in immunofluorescence microscopy of a cell transiently transfected with a nucleic acid encoding at least a portion of the antigenic protein, for example.

The antibodies or antibody fragments include a variable region capable of binding to a cell surface antigen of *S. didolesgii* strain D8. The variable region can be selected from the variable regions of, for example: antibody MH1 ($V_H$=SEQ ID NO: 3; $V_L$=SEQ ID NO: 4); MH3 ($V_H$=SEQ ID NO: 7; $V_L$=SEQ ID NO: 8); MH4 ($V_H$=SEQ ID NO: 9; $V_L$=SEQ ID NO: 10); MH5 ($V_H$=SEQ ID NO: 11; $V_L$=SEQ ID NO: 12); MH6 ($V_H$=SEQ ID NO: 13; $V_L$=SEQ ID NO: 14); MH11 ($V_H$=SEQ ID NO: 23; $V_L$=SEQ ID NO: 24); MH12 ($V_H$=SEQ ID NO: 25; $V_L$=SEQ ID NO: 26); MH14 ($V_H$=SEQ ID NO: 29; $V_L$=SEQ ID NO: 30); MH15 ($V_H$=SEQ ID NO: 31; $V_L$=SEQ ID NO: 32); MH16 ($V_H$=SEQ ID NO: 33; $V_L$=SEQ ID NO: 34); MH17 ($V_H$=SEQ ID NO: 35; $V_L$=SEQ ID NO: 36); MH18 ($V_H$=SEQ ID NO: 37; $V_L$=SEQ ID NO: 38); MH20 ($V_H$=SEQ ID NO: 41; $V_L$=SEQ ID NO: 42); MH21 ($V_H$=SEQ ID NO: 43; $V_L$=SEQ ID NO: 44); MH22 ($V_H$=SEQ ID NO: 45; $V_L$=SEQ ID NO: 46); MH23 ($V_H$=SEQ ID NO: 47; $V_L$=SEQ ID NO: 48); MH24 ($V_H$=SEQ ID NO: 49; $V_L$=SEQ ID NO: 50); MH25 ($V_H$=SEQ ID NO: 51; $V_L$=SEQ ID NO: 52); MH27 ($V_H$=SEQ ID NO: 55; $V_L$=SEQ ID NO: 56); MH28 ($V_H$=SEQ ID NO: 57; $V_L$=SEQ ID NO: 58); MH29 ($V_H$=SEQ ID NO: 59; $V_L$=SEQ ID NO: 60); MH30 ($V_H$=SEQ ID NO: 61; $V_L$=SEQ ID NO: 62); MH31 ($V_H$=SEQ ID NO: 63; $V_L$=SEQ ID NO: 64); MH32 ($V_H$=SEQ ID NO: 65; $V_L$=SEQ ID NO: 66); MH33 ($V_H$=SEQ ID NO: 67; $V_L$=SEQ ID NO: 68); MH34 ($V_H$=SEQ ID NO: 69; $V_L$=SEQ ID NO: 70); MH35 ($V_H$=SEQ ID NO: 71; $V_L$=SEQ ID NO: 72); MH38 ($V_H$=SEQ ID NO: 77; $V_L$=SEQ ID NO: 78); MH39 ($V_H$=SEQ ID NO: 79; $V_L$=SEQ ID NO: 80); MH40 ($V_H$=SEQ ID NO: 81; $V_L$=SEQ ID NO: 82); MH42 ($V_H$=SEQ ID NO: 85; $V_L$=SEQ ID NO: 86); MH45 ($V_H$=SEQ ID NO: 91; $V_L$=SEQ ID NO: 92); MH46 ($V_H$=SEQ ID NO: 93; $V_L$=SEQ ID NO: 94); MH48 ($V_H$=SEQ ID NO: 97; $V_L$=SEQ ID NO: 98), MH49 ($V_H$=SEQ ID NO: 99; $V_L$=SEQ ID NO: 100); MH50 ($V_H$=SEQ ID NO: 101; $V_L$=SEQ ID NO: 102); MH51 ($V_H$=SEQ ID NO: 103; $V_L$=SEQ ID NO: 104); MH55 ($V_H$=SEQ ID NO: 111; $V_L$=SEQ ID NO: 112); MH56 ($V_H$=SEQ ID NO: 113; $V_L$=SEQ ID NO: 114); MH57 ($V_H$=SEQ ID NO: 115; $V_L$=SEQ ID NO: 116); MH58 ($V_H$=SEQ ID NO: 117; $V_L$=SEQ ID NO: 118); MH59 ($V_H$=SEQ ID NO: 119; $V_L$=SEQ ID NO: 120); MH60 ($V_H$=SEQ ID NO: 121; $V_L$=SEQ ID NO: 122); MH62 ($V_H$=SEQ ID NO: 125; $V_L$=SEQ ID NO: 126); MH63 ($V_H$=SEQ ID NO: 127; $V_L$=SEQ ID NO: 128); MH64 ($V_H$=SEQ ID NO: 129; $V_L$=SEQ ID NO: 130); MH65 ($V_H$=SEQ ID NO: 131; $V_L$=SEQ ID NO: 132); MH66 ($V_H$=SEQ ID NO: 133; $V_L$=SEQ ID NO: 134); MH67 ($V_H$=SEQ ID NO: 135; $V_L$=SEQ ID NO: 136); MH68 ($V_H$=SEQ ID NO: 137; $V_L$=SEQ ID NO: 138); MH73 ($V_H$=SEQ ID NO: 147; $V_L$=SEQ ID NO: 148); MH74 ($V_H$=SEQ ID NO: 149; $V_L$=SEQ ID NO: 150) MH75 ($V_H$=SEQ ID NO: 151; $V_L$=SEQ ID NO: 152) MH76 ($V_H$=SEQ ID NO: 153; $V_L$=SEQ ID NO: 154); MH80 ($V_H$=SEQ ID NO: 161; $V_L$=SEQ ID NO: 162); MH82 ($V_H$=SEQ ID NO: 165; $V_L$=SEQ ID NO: 166); MH83 ($V_H$=SEQ ID NO: 187; $V_L$=SEQ ID NO: 188); and MH91 ($V_H$=SEQ ID NO: 183; $V_L$=SEQ ID NO: 184).

In certain embodiments, the variable region is be selected from the variable regions of: antibody MH4 ($V_H$=SEQ ID NO: 9; $V_L$=SEQ ID NO: 10); MH28 ($V_H$=SEQ ID NO: 57; $V_L$=SEQ ID NO: 58); MH58 ($V_H$=SEQ ID NO: 117; $V_L$=SEQ ID NO: 118); and MH91 ($V_H$=SEQ ID NO: 183; $V_L$=SEQ ID NO: 184).

The target antigen can be any *S. didolesgii* strain D8 cell surface antigen or intracellular antigen which becomes accessible to recognition on the cell surface during the bacterial life and death cycles. In some embodiments, the target antigen is one of: amino acid ABC transporter substrate-binding protein, PAAT family (Protein ID: R5Y4K6_9FIRM); elongation factor Tu (Protein ID:

R5YCH3_9FIRM); dTDP-glucose 4,6-dehydratase (Protein ID: R6DWD2_9FIRM); FG-GAP repeat domain-containing protein (plasmid) (Protein ID: A7B574_RUMGV); GTPases—translation elongation factors, partial (Protein ID: WP_009866873.1); putative DNA-binding protein (Protein ID: R5QFF1_9FIRM); short-chain dehydrogenase/reductase SDR (Protein ID: D4M4P2_9FIRM); transposase (Protein ID: R7CQ18_9FIRM); 3-phosphoshikimate 1-carboxyvinyltransferase (protein ID: R6U1K9_9CLOT); ABC transporter, substrate-binding protein, family 5 domain protein (Protein ID: A0A171JU57); MFS transporter (Protein ID: R5YDJ5_9FIRM); IgG-binding protein A (586027 M); and 4-hydroxybenzoate octaprenyltransferase (Protein ID: Q3SLJ4).

Use of a single antibody recognizing a single antigenic epitope is contemplated, as is the use of at least one antibody, where the antibodies can be directed to the same or different antigenic protein epitopes on one or more antigens.

Monoclonal antibodies incorporating the disclosed variable regions can be prepared using well-known preparation procedures, such as those disclosed, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Antibodies and fragments thereof described herein may be humanized using the methods described in, for example, Wright et al., and in the references cited therein, and in Gu et al. (1997, Thrombosis and Hematocyst 77:755-759), and other methods of humanizing antibodies known in the art.

An "antibody" (Ab) shall include, without limitation, an immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

An "antigen binding portion" of an Ab (also called an "antigen-binding fragment") or antigen binding portion thereof refers to one or more sequences of an Ab (full length or fragment of the full length antibody) that retain the ability to bind specifically to the antigen bound by the whole Ab. Examples of an antigen-binding fragment include Fab, $F(ab')_2$, scFv (single-chain variable fragment), Fab', dsFv, sc(Fv)2, and scFv-Fc.

Single chain antibodies (scFv) or Fv fragments and include the disclosed variable regions are also provided, with or without an interconnecting linker.

Functional equivalents of the antibodies of the described herein are also contemplated, and include fragments of antibodies that have the same, or substantially the same, binding characteristics to those of the describe variable regions. The antibody fragments contain all six complementarity determining regions (CDRs) of the variable regions, although fragments containing fewer than all of such regions, such as three, four or five complementarity determining regions, may also functional. The functional equivalents are members of the IgG immunoglobulin class and subclasses thereof, but may be or may combine with any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Exemplary constant regions are gamma 1 (IgG1), gamma 2 (IgG2), gamma 3 (IgG3), and gamma 4 (IgG4). The light chain constant region can be of the kappa or lambda type.

Immunoglobulins can be monovalent, divalent or polyvalent. Monovalent immunoglobulins are dimers (HL) formed of a hybrid heavy chain associated through disulfide bridges with a hybrid light chain. Divalent immunoglobulins are tetramers (H.sub.2L.sub.2) formed of two dimers associated through at least one disulfide bridge.

Vaccines

As described herein, the term "vaccine" (also referred to as an immunogenic composition) refers to a substance or composition that induces an immune response upon inoculation into a subject. In certain embodiments, the vaccine induces an adaptive immune response. The vaccine can be used to induce a protective immune response against *S. didolesgii* strain D8, resulting in the depletion of *S. didolesgii* strain D8 and treating or preventing RA in a subject.

Vaccines of the disclosure induce an immune response to one or more *S. didolesgii* strain D8 antigens. The vaccine can include, for example, an antigen (e.g., a peptide or polypeptide), a nucleic acid encoding an antigen (e.g., an antigen expression vector), or a cell expressing or presenting an antigen or cellular component (e.g., a heat-inactivated cell of *S. didolesgii* strain D8, or a manufactured antigen presenting cell). The vaccine can encode all or part of any peptide target antigen described herein, or an immunologically functional equivalent thereof. In certain embodiments, the vaccine includes an additional immunostimulatory agent or nucleic acids encoding such an agent. Additional immunostimulatory agents include but are not limited to an additional antigen, an immunomodulator, an antigen presenting cell or an adjuvant.

Vaccines can further include additional components such as, for example, a lipid or liposome, or one or more adjuvants. A vaccine described herein and its various components can be prepared and/or administered by the methods described herein, or as would be known to those of skill in the art in light of the present disclosure.

A peptide vaccine can include, but is not limited to, a peptide mixed with adjuvant substances and a peptide which is introduced together with an APC. The most common cells used for the latter type of vaccine are bone marrow and peripheral blood derived dendritic cells, as these cells express costimulatory molecules that help activation of T cells. WO00/06723 discloses a cellular vaccine composition which includes an APC presenting tumor associated antigen peptides. Presenting the peptide can be effected by loading the APC with a polynucleotide (e.g., DNA, RNA) encoding the peptide or loading the APC with the peptide itself.

The vaccine can include one or more peptides, polypeptides, or fragments thereof, or nucleic acid molecules (e.g., DNA or RNA) encoding one or more peptides, polypeptides or fragments thereof, of *S. didolesgii* strain D8. Peptides or polypeptides of *S. didolesgii* strain D8 that may be used include, but are not limited to: amino acid ABC transporter substrate-binding protein, PAAT family (Protein ID: R5Y4K6_9FIRM); elongation factor Tu (Protein ID: R5YCH3_9FIRM); dTDP-glucose 4,6-dehydratase (Protein ID: R6DWD2_9FIRM); FG-GAP repeat domain-containing protein (plasmid) (Protein ID: A7B574_RUMGV); GTPases—translation elongation factors, partial (Protein ID: WP_009866873.1); putative DNA-binding protein (Protein ID: R5QFF1_9FIRM); short-chain dehydrogenase/reductase SDR (Protein ID: D4M4P2_9FIRM); transposase (Protein ID: R7CQ18_9FIRM); 3-phosphoshikimate 1-carboxyvinyltransferase (protein ID: R6U1K9_9CLOT); ABC transporter, substrate-binding protein, family 5 domain protein (Protein ID: A0A171JU57); MFS transporter (Protein ID: R5YDJ5_9FIRM); IgG-binding protein A (586027 M); and 4-hydroxybenzoate octaprenyltransferase (Protein ID: Q3SLJ4).

When a certain peptide or combination of peptides induce an anti-*S. didolesgii* strain D8 immune response upon inoculation into a subject, the peptide or combination of peptides are decided to have anti-*S. didolesgii* strain D8 immunity-inducing effect. The induction of the anti-*S. didolesgii* strain D8 immunity by a peptide or combination of peptides can be detected by observing in vivo or in vitro the response of the immune system in the host against the peptide.

The vaccine can include an inactivated or killed *S. didolesgii* strain D8 bacterium. Inactivated/killed generally refers to infectious agents (e.g., bacteria, viruses, other microorganisms or agents) that are not capable of reproducing or causing disease (i.e., avirulent). Inactivated bacterial preparations may be called bacterins. The inactivated/killed agents are able to stimulate an immune response when administered to a subject, in the context of a vaccine composition, for example. In contrast to inactivated vaccines, live vaccines and live attenuated vaccines, for example, are able to replicate and generally do so once they are administered to a subject.

The vaccine can include substantially less than all of a bacterium (i.e., a subunit vaccine. For example, subunit vaccines may contain single or a few recombinant protein antigens from a bacterium. Inactivated or killed vaccines generally include more of a bacterium, for example, than does a subunit vaccine.

Agents for inclusion in an inactivated or killed vaccine may be grown, purified or semi-purified, inactivated, and then formulated into a vaccine composition. Bacteria may be grown on cell free, serum-free, protein-free, synthetic medium and the like, using commonly known methods for growth of pure bacterial cultures. Often, bacteria are grown in liquid cultures. The bacteria may be purified, semi-purified, and/or concentrated. For example, bacteria grown in liquid culture may be subject to relatively low-speed centrifugation, the culture medium decanted, and the bacterial pellet re-suspended in buffer.

The bacteria may be killed or inactivated using a variety of methods. In one example, the bacteria may be treated with various chemicals for various periods of time to render the agents incapable of replication, but still retaining at least some ability to stimulate an immune response (i.e., immunogenicity) when administered to a subject.

An anti-*S. didolesgii* strain D8 response can be induced by administering a vaccine described herein, and the induction of an anti-*S. didolesgii* strain D8 response enables treatment and prevention of RA in a subject.

Antibiotics

Antibiotics capable of diminishing or eliminating a population of *S. didolesgii* strain D8 in a subject are provided. In some embodiments, the antibiotic is non-absorbable or poorly absorbable, resulting in the antibiotic to exert its effects primarily within the gastrointestinal tract. Non-absorbable and poorly absorbable antibiotics include but are not limited to norfloxacin, rifaximin, gentamicin, vancomycin, nystatin, neomycin, colistin, and kanamycin.

Antibiotics directed to *S. didolesgii* strain D8 can reduce the amount or activity of *S. didolesgii* strain D8 in a subject. Dosages for appropriate antibiotics can be determined by those skilled in the art, and will generally be comparable to standard dosages for each given antibiotic. In some embodiments, a compound or treatment method may include a single antibiotic, or a combination of two or more antibiotics.

*S. didolesgii* Strain D8 Inhibitors

In various embodiments, provided herein are inhibitors of *S. didolesgii* strain D8 activity. *S. didolesgii* strain D8 inhibitors can include, for example, a protein, a peptide, a peptidomimetic, an antibody, a ribozyme, a small molecule chemical compound, a nucleic acid molecule, a vector, an antisense nucleic acid molecule, a CRISPR-associated enzyme or guide RNA, and pre-biotics. In certain embodiments, these agents reduce the activity of *S. didolesgii* strain D8 in a subject.

The agents provided include inhibitors of *S. didolesgii* strain D8 proteins and/or genes, where the inhibitor reduces *S. didolesgii* strain D8 activity involved in inducing an inflammatory response in the host tissue of a subject. An inhibitor encompasses any chemical compound that decreases the amount or activity of *S. didolesgii* strain D8 associated with an inflammatory response.

In some embodiments, the *S. didolesgii* strain D8 inhibitor inhibits production of an indole by, for example, blocking or otherwise modifying an indole-related pathway. As used herein, the term "indole inhibitor" refers to inhibitors capable of inhibiting production of an indole by any means, including blocking or otherwise modifying an indole-related pathway, as well as inhibitors capable of blocking the function or activity of an indole-containing compound. "Indole-related pathway" refers to any of the pathways involved in producing an indole-containing compound or utilizes an indole-containing compound as an intermediary.

In some embodiments, the inhibitor can be a small molecule inhibitor. Small molecule inhibitors include tryptophanase inhibitors. Tryptophanase inhibitors include, for example, S-phenylbenzoquinone-L-tryptophan, alpha-amino-2-(9,10-anthraquinone)-propanoic acid, L-tryptophane-ethylester, N-acetyl-L-tryptophan.

In some embodiments, the inhibitor can be a nucleic acid inhibitor. The nucleic acid inhibitor can be an antisense molecule or aptamer which inhibits one or more *S. didolesgii* strain D8 proteins or genes, such as one or more components of an indole-related pathway. In some embodiments, the nucleic acid comprises a promoter/regulatory sequence such that the promoter/regulatory sequence is capable of directing expression of the nucleic acid or increasing or decreasing stability of the nucleic acid. Thus, also contemplated herein are expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York).

siRNA can be used to inhibit one or more *S. didolesgii* strain D8 proteins or genes.

Vectors including an siRNA or antisense polynucleotide are provided. The vectors can encode a short hairpin RNA (shRNA) inhibitor directed against a target mRNA, thereby decreasing expression of the target. The encoded shRNA can be expressed by a cell, and then processed into siRNA (e.g., the cells can possess native enzymes (e.g., dicer) that cleave the shRNA to form siRNA).

The siRNA, shRNA, or antisense polynucleotide can be cloned into a number of types of vectors. For expression of the siRNA or antisense polynucleotide, at least one module in each promoter functions to position the start site for RNA synthesis.

Expression vectors to be introduced into a cell can also include a selectable marker gene or a reporter gene, or both, to facilitate identification and selection of expressing cells. Therefore, also provided are vectors including a nucleotide sequence contemplated herein. The choice of the vector will depend on the host cell in which it is to be subsequently introduced. In a particular embodiment, the vector is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Antisense molecules and their use for inhibiting RNA molecules are well known. Antisense nucleic acids are DNA or RNA molecules that are complementary to at least a portion of a specific target mRNA molecule (Weintraub, 1990, Scientific American 262:40). In the cell, antisense nucleic acids hybridize to the corresponding mRNA, forming a double-stranded molecule thereby inhibiting the translation of genes.

Certain embodiments provide for inhibition of one or more genes of *S. didolesgii* strain D8 through use of a genome editing system. A series of programmable nuclease-based genome editing technologies have developed (see, for example, Hsu et al., Cell 157, Jun. 5, 2014 1262-1278), including, but not limited to, meganucleases, zinc finger nucleases (ZFNs), transcription activator-like effector-based nucleases (TALENs) and CRISPR-Cas systems (see e.g. Platt et al., Cell 159(2), 440-455 (2014); Shalem et al., Science 3 84-87 (2014); and Le Cong et al., Science 339, 819 (2013)) or alternative CRISPR systems. Genome editing systems have a wide variety of utilities including modifying (e.g., deleting, inserting, translocating, inactivating, activating, repressing, altering methylation, transferring specific moieties) a target polynucleotide in a multiplicity of cell types.

Certain embodiments provide a CRISPR-Cas system, where a guide RNA (gRNA) targeted to a target nucleic acid sequence, and a CRISPR-associated (Cas) peptide form a complex to induce mutations within the targeted nucleic acid sequence. A CRISPR complex contemplated herein provides an effective means for modifying a target nucleic acid sequence, such as that of a *S. didolesgii* strain D8 gene involved in an indole-related pathway. In some embodiments, the CRISPR-Cas is delivered via a phage that infect *S. didolesgii* strain D8 (see, for example, Fage et al., Current Opinion in Biotechnology, April 2021, 68:174-180, and Lam et al., bioRxiv 2020.07.09.193847; doi: //doi.org/10.1101/2020.07.09.193847). This technology can be adapted to reduce a population of *S. didolesgii* strain D8 in a subject or eliminate a population of *S. didolesgii* strain D8 in a subject.

In some embodiments, provided herein is a Cas peptide or Cas-derived peptide and a gRNA targeted to a *S. didolesgii* strain D8 gene, coding sequence, or regulatory sequence. In one embodiment, a nucleic acid molecule encoding a Cas peptide or Cas-derived peptide is provided. In one embodiment, the nucleic acid molecule encoding a gRNA targeted to an *Enterococcus* sp. or host gene, coding sequence, or regulatory sequence.

The target polynucleotide can be a DNA molecule. DNA molecules include, but are not limited to, genomic DNA molecules, extrachromosomal DNA molecules, conjugative plasmids and exogenous DNA molecules. In one embodiment, the target polynucleotide is an RNA molecule.

Inhibitors also include isolated peptide inhibitors that inhibit one or more *S. didolesgii* strain D8 proteins or genes.

Treatment Methods

Methods are provided that reduce a population of *S. didolesgii* strain D8 in a subject, eliminate a population of *S. didolesgii* strain D8 in a subject, inhibit an indole-containing compound produced by *S. didolesgii* strain D8, inhibit an indole-related pathway in *S. didolesgii* strain D8, inhibit or prevent an immune response by a subject to *S. didolesgii* strain D8; elicit a protective immune response in a subjected against infection by *S. didolesgii* strain D8, or any combination thereof. Such methods can be useful in, for example, preventing rheumatoid arthritis in subject, delaying onset of rheumatoid arthritis in a subject, treating rheumatoid arthritis in a subject, or ameliorating at least one symptom of rheumatoid arthritis in a subject.

The methods can be executed by administering to a subject an effective amount of a composition described herein.

The therapeutic agents and compositions described herein can be administered prophylactically or therapeutically to subjects at risk of (or susceptible to) developing RA, those presenting with preclinical RA, or those subjects diagnosed with RA. Novel methods for identifying such subjects are provided herein, and include detection of *S. didolesgii* strain D8 or antibodies against *S. didolesgii* strain D8 in a subject. In some embodiments, the treatment methods described can be applied to subjects identified as being at risk of developing RA, those having preclinical RA, and those having RA using standard clinical methods. Prophylactic administration occurs prior to the manifestation of overt clinical symptoms of RA, such that RA is prevented or alternatively delayed in its progression. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

Administration of the agents and compositions can be achieved in a number of ways using methods known in the art, including systemic administration (e.g. enteral or parenteral administration), intradermal delivery, intramuscular delivery, subcutaneous delivery, inhalation, and intranasal delivery.

The agents and compositions described herein can be administered to a subject alone, or in conjunction with one or more agents, such as those traditionally utilized in the treatment of RA. These agents include but are not limited to non-steroidal anti-inflammatory drugs, corticosteroids, disease-modifying antirheumatic drugs, and biologic response modifiers.

Examples of suitable non-steroidal anti-inflammatory drugs include: ibuprofen; naproxen sodium; celecoxib; diclofenac; fenoprofen; flurbiprofen; indomethacin; ketorolac; mefenamic acid; meloxicam; oxaprozin; piroxicam; and sulindac.

Examples of suitable corticosteroids include: prednisone; bethamethasone; and prednisolone; triamcinolone; methylprednisolone; and dexamethasone.

Examples of suitable disease-modifying antirheumatic drugs include: methotrexate; leflunomide; hydroxychloroquine; and sulfasalazine.

Examples of suitable biologic response modifiers include: abatacept and biosimilars thereof; adalimumab and biosimilars thereof; anakinra and biosimilars thereof; baricitinib; certolizumab and biosimilars thereof; etanercept and biosimilars thereof; golimumab and biosimilars thereof; infliximab and biosimilars thereof; rituximab and biosimilars thereof; sarilumab and biosimilars thereof; tocilizumab and biosimilars thereof; and tofacitinib.

The agents and compositions may be administered to a subject as frequently as several times daily, or it may be administered less frequently, such as once a day, once a week, once every two weeks, once a month, or even less frequently, such as once every several months or even once a year or less. The frequency of the dose will be readily determinable by the skilled artisan and will depend upon any number of factors, such as, but not limited to, the type and severity of the disease being treated.

In some embodiments, administration of an immunogenic composition or vaccine described herein can be performed by single administration or boosted by multiple administrations.

Methods of Detecting *S. didolesgii* Strain D8

Provided herein are methods for detecting the presence of *S. didolesgii* strain D8 in a biological sample obtained from a subject. Also provided are methods for detecting the presence of one or more antibodies against *S. didolesgii* strain D8 in a subject.

Direct sequence analysis can be used to detect a bacterial nucleic acid (e.g., a genome) of interest. A sample including DNA or RNA can be used, and PCR or other appropriate methods can be used to amplify all or a fragment of the nucleic acid, and/or its flanking sequences, if desired. The bacterial nucleic acid, or a fragment thereof, is determined, using standard methods. The presence of *S. didolesgii* strain D8 can detected utilizing a genomic approach, where bacterial genomic DNA isolated from a biological sample is analyzed to determine its genetic identity. The genomic approach can involve, for example, PCR analysis or whole genome sequencing (WGS). Where WGS sequencing is utilized, methods can include a PCR step or a multiple displacement amplification step.

Presence of *S. didolesgii* strain D8 can be detected by identifying the presence in the biological sample of *S. didolesgii* strain D8 genomic DNA. A contig representing the genomic sequence of *S. didolesgii* strain D8 is provided in SEQ ID NO: 2. An alignment of experimental sequences to SEQ ID NO: 2 can reveal the presence of *S. didolesgii* strain D8 in the sample. Those of skill in the art, having the benefit of this disclosure, including the accompanying sequence listing, will readily be able to identify experimental genomic sequences as belonging to *S. didolesgii* strain D8, if present in a sample. *S. didolesgii* strain D8 is also being maintained in the lab of inventor Kuhn. A sample of *S. didolesgii* strain D8 will deposited with a depository in accordance with the Budapest Treaty. The instant disclosure will be updated with details of the deposit once available. Those of skill in the art will be able to compare the deposited *S. didolesgii* strain D8 to bacteria—and their genomes—identified in biological samples.

In another embodiment, arrays of oligonucleotide probes that are complementary to target microbial nucleic acid sequences can be used to detect and identify microbial nucleic acids.

Biological samples can include, for example, fecal samples, rectal swabs, intestinal biopsies, along with samples from other mucosal or cutaneous sites.

Hybridization methods, such as Southern analysis, Northern analysis, or in situ hybridizations, can be used (see Current Protocols in Molecular Biology, Ausubel, F. et al., eds., John Wiley & Sons, including all supplements). For example, the presence of nucleic acid from a particular type of bacteria (e.g., *S. didolesgii* strain D8) can be determined by hybridization of nucleic acid to a nucleic acid probe. A "nucleic acid probe," as used herein, can be a DNA probe or an RNA probe. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate target RNA or DNA. The hybridization sample is maintained under conditions which are sufficient to allow specific hybridization of the nucleic acid probe to RNA or DNA. Specific hybridization can be performed under high stringency conditions or moderate stringency conditions, as appropriate. In one embodiment, the hybridization conditions for specific hybridization are high stringency. More than one nucleic acid probe can also be used concurrently in this method. Specific hybridization of any one of the nucleic acid probes is indicative of the presence of the particular type of bacteria of interest, as described herein.

In some embodiments, methods of detecting *S. didolesgii* strain D8 in a biological sample include increasing the relative abundance of bacteria from Lachnospiraceae, Ruminococcaceae, or both Lachnospiraceae and Ruminococcaceae in a fraction of the biological sample. This involves selectively isolating bacteria from Lachnospiraceae, Ruminococcaceae, or both Lachnospiraceae and Ruminococcaceae, to the exclusion of other bacteria. This process results in a high proportion of Lachno/Rumino relative to other bacteria, making the detection of *S. didolesgii* strain D8 in the sample easier. The relative abundance can be increased by contacting the sample from the subjected with the variable region of one or more antibodies disclosed and described herein. For example, the enriched fraction can be contacted with an antibody, or antigen binding fragment thereof, chosen from MH1 ($V_H$=SEQ ID NO: 3; $V_L$=SEQ ID NO: 4); MH3 ($V_H$=SEQ ID NO: 7; $V_L$=SEQ ID NO: 8); MH4 ($V_H$=SEQ ID NO: 9; $V_L$=SEQ ID NO: 10); MH5 ($V_H$=SEQ ID NO: 11; $V_L$=SEQ ID NO: 12); MH6 ($V_H$=SEQ ID NO: 13; $V_L$=SEQ ID NO: 14); MH11 ($V_H$=SEQ ID NO: 23; $V_L$=SEQ ID NO: 24); MH12 ($V_H$=SEQ ID NO: 25; $V_L$=SEQ ID NO: 26); MH14 ($V_H$=SEQ ID NO: 29; $V_L$=SEQ ID NO: 30); MH15 ($V_H$=SEQ ID NO: 31; $V_L$=SEQ ID NO: 32); MH16 ($V_H$=SEQ ID NO: 33; $V_L$=SEQ ID NO: 34); MH17 ($V_H$=SEQ ID NO: 35; $V_L$=SEQ ID NO: 36); MH18 ($V_H$=SEQ ID NO: 37; $V_L$=SEQ ID NO: 38); MH20 ($V_H$=SEQ ID NO: 41; $V_L$=SEQ ID NO: 42); MH21 ($V_H$=SEQ ID NO: 43; $V_L$=SEQ ID NO: 44); MH22 ($V_H$=SEQ ID NO: 45; $V_L$=SEQ ID NO: 46); MH23 ($V_H$=SEQ ID NO: 47; $V_L$=SEQ ID NO: 48); MH24 ($V_H$=SEQ ID NO: 49; $V_L$=SEQ ID NO: 50); MH25 ($V_H$=SEQ ID NO: 51; $V_L$=SEQ ID NO: 52); MH27

($V_H$=SEQ ID NO: 55; $V_L$=SEQ ID NO: 56); MH28 ($V_H$=SEQ ID NO: 57; $V_L$=SEQ ID NO: 58); MH29 ($V_H$=SEQ ID NO: 59; $V_L$=SEQ ID NO: 60); MH30 ($V_H$=SEQ ID NO: 61; $V_L$=SEQ ID NO: 62); MH31 ($V_H$=SEQ ID NO: 63; $V_L$=SEQ ID NO: 64); MH32 ($V_H$=SEQ ID NO: 65; $V_L$=SEQ ID NO: 66); MH33 ($V_H$=SEQ ID NO: 67; $V_L$=SEQ ID NO: 68); MH34 ($V_H$=SEQ ID NO: 69; $V_L$=SEQ ID NO: 70); MH35 ($V_H$=SEQ ID NO: 71; $V_L$=SEQ ID NO: 72); MH38 ($V_H$=SEQ ID NO: 77; $V_L$=SEQ ID NO: 78); MH39 ($V_H$=SEQ ID NO: 79; $V_L$=SEQ ID NO: 80); MH40 ($V_H$=SEQ ID NO: 81; $V_L$=SEQ ID NO: 82); MH42 ($V_H$=SEQ ID NO: 85; $V_L$=SEQ ID NO: 86); MH45 ($V_H$=SEQ ID NO: 91; $V_L$=SEQ ID NO: 92); MH46 ($V_H$=SEQ ID NO: 93; $V_L$=SEQ ID NO: 94); MH48 ($V_H$=SEQ ID NO: 97; $V_L$=SEQ ID NO: 98), MH49 ($V_H$=SEQ ID NO: 99; $V_L$=SEQ ID NO: 100); MH50 ($V_H$=SEQ ID NO: 101; $V_L$=SEQ ID NO: 102); MH51 ($V_H$=SEQ ID NO: 103; $V_L$=SEQ ID NO: 104); MH55 ($V_H$=SEQ ID NO: 111; $V_L$=SEQ ID NO: 112); MH56 ($V_H$=SEQ ID NO: 113; $V_L$=SEQ ID NO: 114); MH57 ($V_H$=SEQ ID NO: 115; $V_L$=SEQ ID NO: 116); MH58 ($V_H$=SEQ ID NO: 117; $V_L$=SEQ ID NO: 118); MH59 ($V_H$=SEQ ID NO: 119; $V_L$=SEQ ID NO: 120); MH60 ($V_H$=SEQ ID NO: 121; $V_L$=SEQ ID NO: 122); MH62 ($V_H$=SEQ ID NO: 125; $V_L$=SEQ ID NO: 126); MH63 ($V_H$=SEQ ID NO: 127; $V_L$=SEQ ID NO: 128); MH64 ($V_H$=SEQ ID NO: 129; $V_L$=SEQ ID NO: 130); MH65 ($V_H$=SEQ ID NO: 131; $V_L$=SEQ ID NO: 132); MH66 ($V_H$=SEQ ID NO: 133; $V_L$=SEQ ID NO: 134); MH67 ($V_H$=SEQ ID NO: 135; $V_L$=SEQ ID NO: 136); MH68 ($V_H$=SEQ ID NO: 137; $V_L$=SEQ ID NO: 138); MH73 ($V_H$=SEQ ID NO: 147; $V_L$=SEQ ID NO: 148); MH74 ($V_H$=SEQ ID NO: 149; $V_L$=SEQ ID NO: 150) MH75 ($V_H$=SEQ ID NO: 151; $V_L$=SEQ ID NO: 152) MH76 ($V_H$=SEQ ID NO: 153; $V_L$=SEQ ID NO: 154); MH80 ($V_H$=SEQ ID NO: 161; $V_L$=SEQ ID NO: 162); MH82 ($V_H$=SEQ ID NO: 165; $V_L$=SEQ ID NO: 166); MH83 ($V_H$=SEQ ID NO: 187; $V_L$=SEQ ID NO: 188); and MH91 ($V_H$=SEQ ID NO: 183; $V_L$=SEQ ID NO: 184). In certain embodiments, the enriched fraction can be contacted with an antibody, or antigen-binding fragment thereof, chosen from MH4 ($V_H$=SEQ ID NO: 9; $V_L$=SEQ ID NO: 10); MH28 ($V_H$=SEQ ID NO: 57; $V_L$=SEQ ID NO: 58); MH58 ($V_H$=SEQ ID NO: 117; $V_L$=SEQ ID NO: 118); and MH91 ($V_H$=SEQ ID NO: 183; $V_L$=SEQ ID NO: 184).

The bacteria can then be released from the monoclonal antibodies to allow for further analysis.

In other embodiments, the presence of one or more antibodies against *S. didolesgii* strain D8 is detected in a serum or fecal sample of a subject. This can be done by contacting the serum or fecal sample from the subject with isolated bacteria of *S. didolesgii* strain D8, or one or more isolated antigens thereof. Binding of serum or fecal antibodies to the isolated *S. didolesgii* strain D8 or its isolated antigens can then be detected.

Also provided are methods for preparing a sample fraction for detection of *S. didolesgii* strain D8 in a subject. Such methods generally include contacting a sample (e.g., fecal sample, fecal swab, or intestinal biopsy) with one or more monoclonal antibodies or one or more monoclonal antibody fragments having a variable region as described herein. After contacting the sample with the one or more monoclonal antibodies or one or more monoclonal antibody fragments, the resulting fraction will include an increased relative abundance of bacteria from Lachnospiraceae, Ruminococcaceae, or both Lachnospiraceae and Ruminococcaceae in the sample fraction. Such methods can be set up similarly to a traditional immunoprecipitation assay, which will provide for the "pull down" of the target bacteria. After achieving the enriched sample fraction, the bacteria can be released from the one or more monoclonal antibodies or one or more antibody fragments.

Methods of Diagnosis

Various embodiments provide for methods of diagnosing a subject as having, or as being at risk for developing, rheumatoid arthritis. A subject can be diagnosed as having, or as being at risk for developing, rheumatoid arthritis by detecting the presence of *S. didolesgii* strain D8 or antibodies against *S. didolesgii* strain D8 in a subject. Presence of *S. didolesgii* strain D8 or antibodies against *S. didolesgii* strain D8 can be detected in accordance with the methods described herein.

In some embodiments methods for diagnosing a subject as having, or as being at risk for developing, rheumatoid arthritis further include effectuating a treatment regimen on a subject diagnosed as having, or at risk of having, RA. The method can include diagnosing a subject with RA or at risk of developing RA based upon the detection of *S. didolesgii* strain D8 or antibodies against *S. didolesgii* strain D8 in a subject, and administering a treatment regimen described herein to the subject to treat or otherwise prevent RA in the subject.

Kits

Also provided are kits useful in carrying out the methods of the disclosure. Such kits comprise components useful in any of the methods described herein, including for example, hybridization probes or primers (e.g., labeled probes or primers), reagents for detection of labeled molecules, means for amplification of nucleic acids, means for analyzing a nucleic acid sequence, antibodies, and instructional materials. For example, in one embodiment, the kit comprises components useful for analysis of a bacterial nucleic acid of interest present in a biological sample obtained from a subject. In one embodiment, the kit comprises components for detecting one or more of the bacterial nucleic acids of interest present in a biological sample derived from a subject.

EXAMPLES

The materials, methods, and embodiments described herein are further defined in the following Examples. Certain embodiments are defined in the Examples herein. It should be understood that these Examples, while indicating certain embodiments, are given by way of illustration only. From the disclosure herein and these Examples, one skilled in the art can ascertain the essential characteristics of this invention, and without departing from the spirit and scope thereof, can make various changes and modifications of the invention to adapt it to various usages and conditions.

Experimental Example 1

Plasmablasts are a subset of circulating B cells, that are circulating components of ongoing local immune responses and could link immune responses at the mucosa with the joint. Having previously identified in individuals at risk for RA a population of circulating plasmablasts that belong to dual IgA/IgG clonal families, the following studies were undertaken prepare monoclonal antibodies from plasmablasts to study and identify mucosal and systemic targets of the antibodies.

Plasmablast monoclonal antibodies (mAb) were derived from flow sorting circulating plasmablasts from 2 individuals positive for antibodies against cyclic citrullinated peptide (CPP+) and diagnosed with rheumatoid arthritis (RA) less than 1 year prior to blood draw, and from 4 asymptomatic individuals who were CPP+ or RF+ (rheumatoid factor) and thus at risk for future RA onset. Variable light and heavy chain sequences from dual IgG and IgA clonal families identified in the plasmablasts were sequenced, cloned into a mouse IgG2a backbone, and expressed. A total of 94 mAbs were expressed (M1-M94).

The mAbs were utilized in assays to detect antigen reactivity. The mAbs were applied to a synovial antigen array representing a range of citrullinated and non-citrullinated antigens known to be relevant to RA. The mAbs targeted several citrullinated autoantigens, validating their identity as autoantibodies. The heatmap of FIG. 1A summarizes the relative reactivity between mAb and antigen, from no reactivity (blue) to high reactivity (red). The mAbs appearing in the heatmap of FIG. 1A, from top to bottom, are anti-IL8 as an assay control, plasmablast-derived antibodies MH1 through MH94, assay control F57m, and assay control B29m.

Figure 1B:
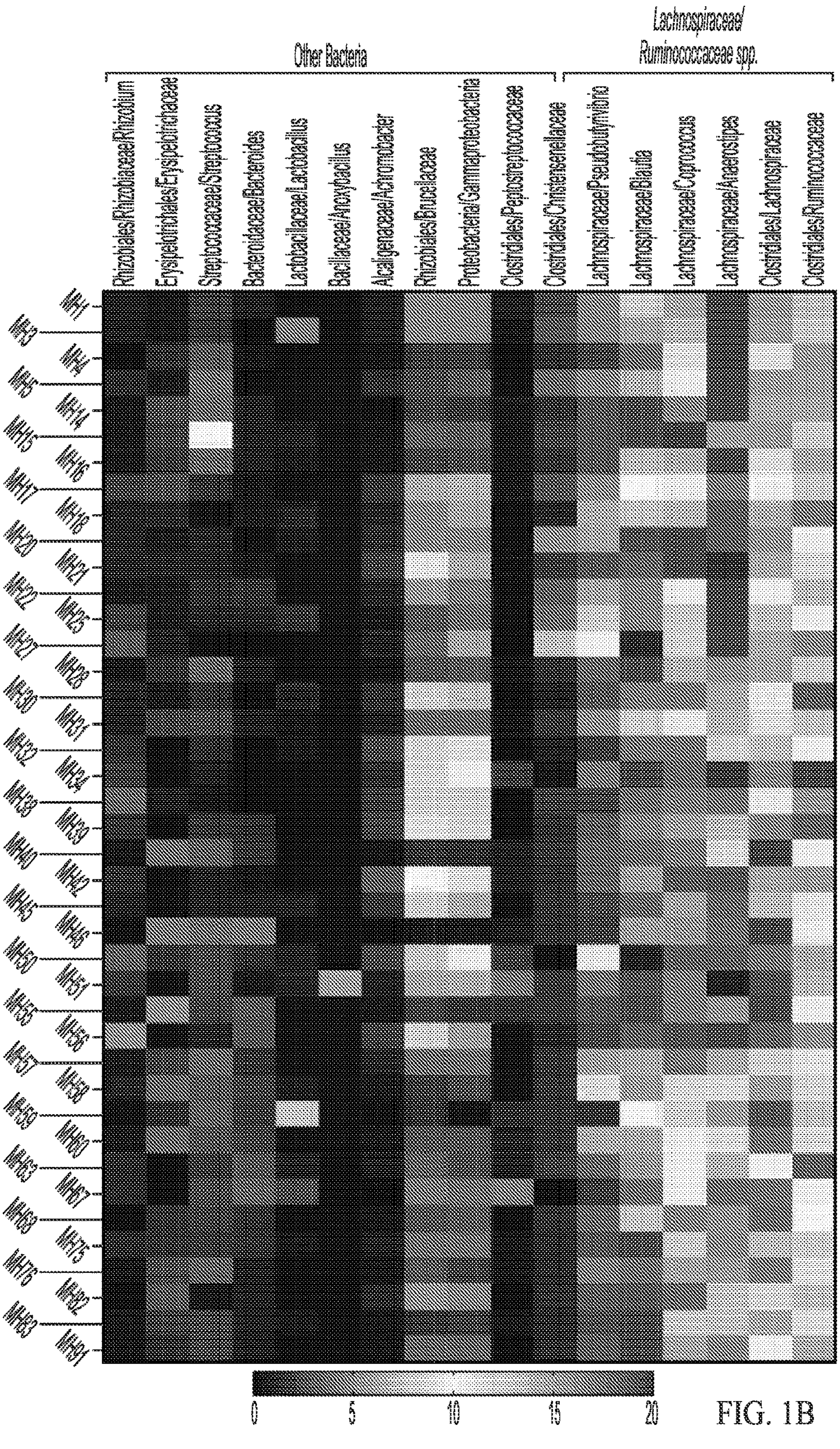
FIG. 1B is a heatmap representing relative reactivity abundance of bacterial taxa identified following flow cytometry utilizing binding by select mAbs from FIG. 1A.
Figure 1C:
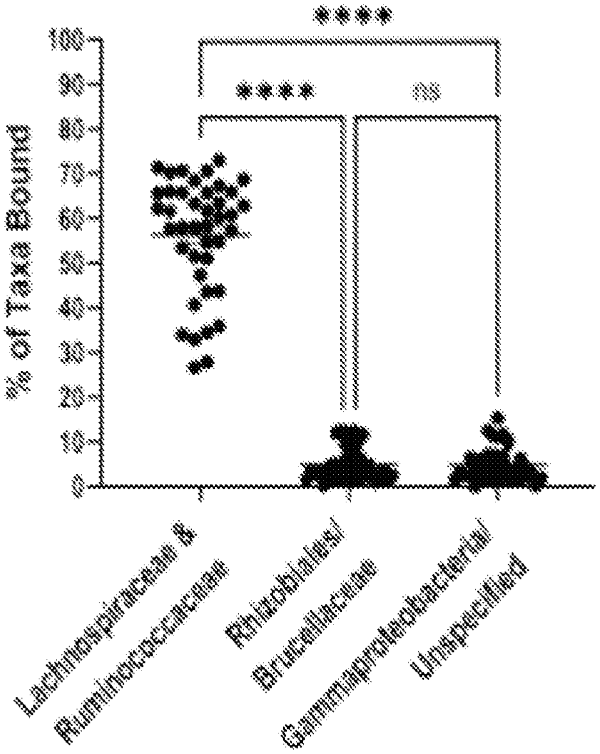
FIG. 1C depicts data of the three most bound taxa from the bound fraction of each plasmablast mAb, represented out of the total bacteria bound by each mAb. ****=P<0.0001 and ns=not significant.

To test whether any plasmablast mAbs target intestinal bacteria and to define such targets, the following study was performed. Fecal samples from 20 individuals (healthy control n=5, at-risk for future RA n=8, and classified RA m=5) were pooled, and contacted with the mAbs to test reactivity. The pooled sample approach resulted in a broadly representative commensal intestinal bacteria pool, and limited internal biases and variability. Antibody-labeled bacteria were flow sorted using a PE-labeled anti-murine IgG2a Fc antibody. DNA was harvested from sorted bacteria, the V3V4 16s rRNA regions were amplified and sequenced, and the sequences were aligned to determine bacterial taxa. The heatmap of FIG. 1B summarizes the relative abundance of taxa within the mAb-bound fraction, from no taxa (blue) to high abundance (red). The mAbs bound to many bacterial antigens, particularly in the closely related families Lachnospiraceae and Ruminococcaceae. Indeed, >50% of the total bacteria bound by all of the bacteria-binding mAbs combined were from families Lachnospiraceae and Ruminococcaceae. See, FIG. 1C. The mAbs appearing in the heatmap of FIG. 1B, from top to bottom, are plasmablast-derived antibodies MH1, MH3, MH4, MH5, MH14, MH15, MH16, MH17, MH18, MH20, MH21, MH22, MH25, MH27, MH28, MH30, MH31, MH32, MH34, MH38, MH39, MH40, MH42, MH45, MH46, MH50, MH51, MH55, MH56, MH57, MH58, MH59, MH60, MH63, MH67, MH68, MH75, MH76, MH82, MH83, and MH91.

The following plasmablast-derived mAbs reacted with bacteria in the pooled fecal sample: MH1, MH3, MH4, MH5, MH6, MH11, MH12, MH14, MH15, MH16, MH17, MH18, MH20, MH21, MH22, MH23, MH24, MH25, MH27, MH28, MH29, MH30, MH31, MH32, MH33, MH34, MH35, MH38, MH39, MH40, MH42, MH45, MH46, MH48, MH49, MH50, MH51, MH55, MH56, MH57, MH58, MH59, MH60, MH62, MH63, MH64, MH65, MH66, MH67, MH68, MH73, MH74, MH75, MH76, MH80, MH82, MH83, and MH91.

Table 1 summarizes the data of FIGS. 1A and 1B, demonstrating mAbs derived from circulating plasmablasts in individuals at-risk for developing RA target both citrullinated autoantigens and bacterial antigens at a high frequency. The table provides the number of mAbs studied, how many bound synovial antigens (>100 relative units by microarray), and how many bound bacteria (>2 standard deviations above background binding of a primary against *Borrelia burgdorferi*).

TABLE 1

| | # mAbs generated | % synovial antigen reactive | % bacteria reactive |
|---|---|---|---|
| 4 at-risk individuals | 78 | 100 | 69.2 |
| 2 early RA individuals | 16 | 100 | 25 |
| TOTAL | 94 | 100 | 62.7 |

Experimental Example 2

Figure 2A:
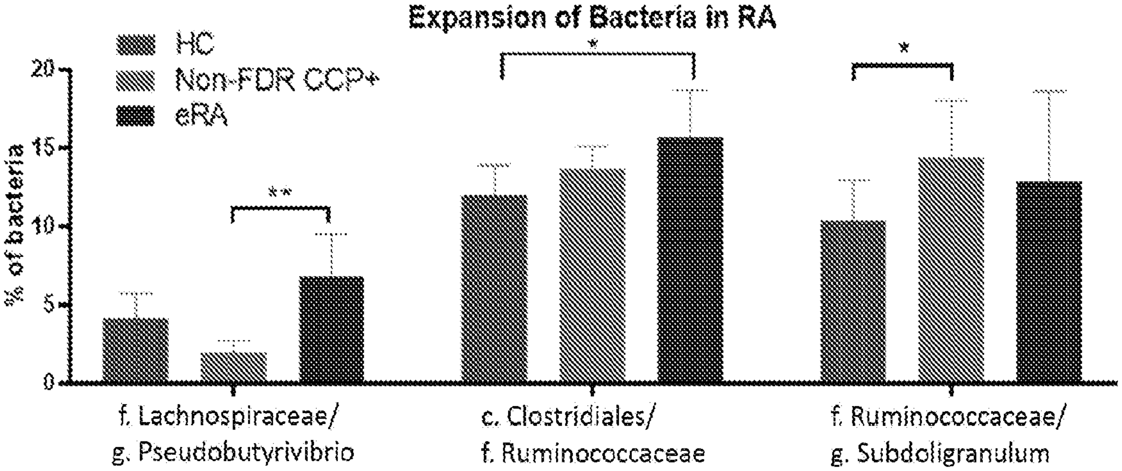
FIG. 2A is a bar chart illustrating an observed expansion of bacteria in RA. HC=healthy controls; Non-FDR (CCP+) =at risk for RA as defined as being asymptomatic but serum CPP+ and without a first-degree relative (FDR) with RA; eRA=early RA (<1 year from diagnosis). *=P<0.05; **=P<0.01 with FDR<0.1.
Figure 2B:
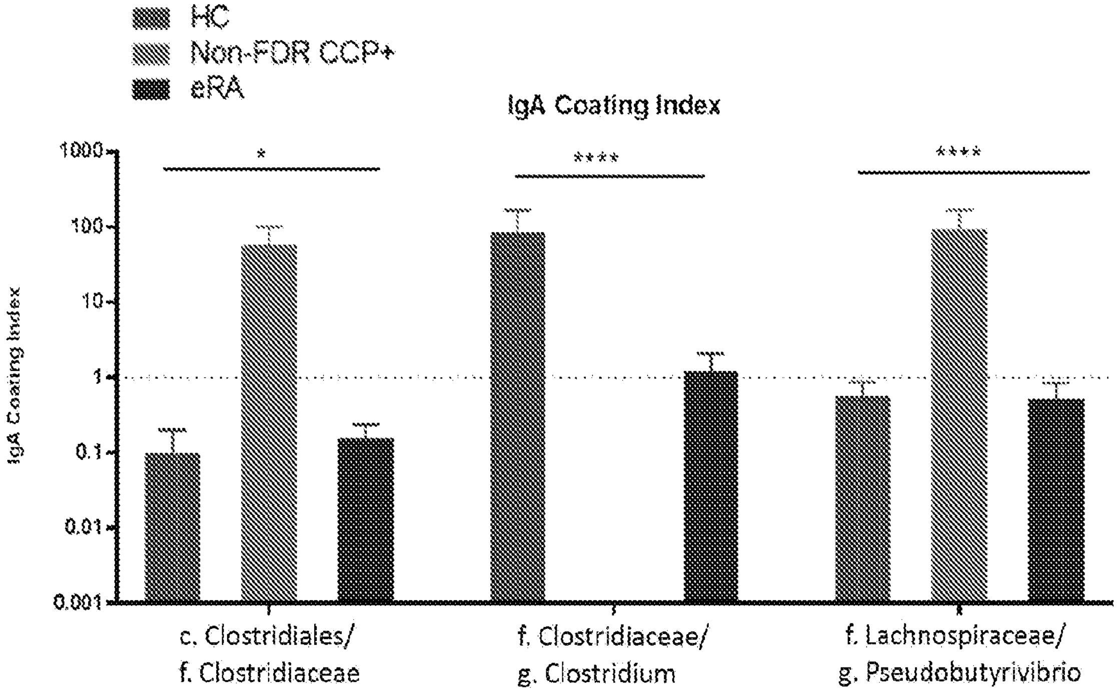
FIG. 2B is a bar chart illustrating the IgA coating index of various bacteria. HC=healthy controls; Non-FDR (CCP+) =at risk for RA as defined as being asymptomatic but serum CPP+ and without a first degree relative (FDR) with RA; eRA=early RA (<1 year from diagnosis). *=P<0.05; ****=P<0.0001 and FDR<0.1.

Taxa within class Clostridiales and families Lachnospiraceae and Ruminococcaceae in the feces of individuals at risk for RA and with early RA were examined. FIGS. 2A and 2B summarize the results from healthy controls (HC, N=16), individuals at-risk for RA defined as being asymptomatic but serum CCP+ and without a first degree relative (FDR) with RA (Non-FDR CCP+, N=12), and individuals with early RA (eRA) as defined as being <1 year from diagnosis (N=13). Fecal bacteria from these individuals underwent sequencing of the V3V4 region of bacterial 16S rRNA.

As depicted in FIG. 2A, statistically significant changes, as determined by Wilcoxon rank tests, were observed in the total relative abundance of taxa identified by class (c), family (f), or genus (g) within each group (*=P<0.05, and **=P<0.01 with FDR<0.1).

Endogenously IgA-coated bacteria were sorted by flow cytometry using a PE-labeled anti-human IgA antibody. Bacterial DNA was extracted, amplified, and sequenced using the V3V4 region of bacterial 16S rRNA. The IgA coating index was calculated as the % abundance in the IgA+ fraction divided by the % abundance in the IgA- fraction. Results summarizing the IgA coating index of taxa identified by class (c), family (f), or genus (g) are depicted in FIG. 2B. Statistically significant changes were determined by Wilcoxon rank test (*=P<0.05 and ****=P<0.0001 and FDR<0.1).

Taken together, these results indicate that bacteria of class Clostridiales, including its families Lachnospiraceae and Ruminococcaceae, are expanded in the fecal microbiome of individuals at risk for and with RA, and are preferentially targeted by endogenous fecal IgA.

Experimental Example 3

To investigate immune responses to Lachnospiraceae and Ruminococcaceae in RA, primary bacterial isolates were established from an at-risk individual with >40% abundance of of families Lachnospiraceae (Lachno) and Ruminococcaceae (Rumino) in their feces. Feces from the at-risk individual was homogenized in mega media that supports anaerobic growth. The homogenate was serially diluted to an estimated one cell per well in a 96-well plate, and was cultured under anaerobic conditions. Plates were incubated at 37° C. in an anaerobic chamber for 4 days when growth was observed. Wells were screened by PCR for amplification of 16S rRNA specific to Lachno/Rumino families. Those that amplified by PCR were then subcloned by serial dilution and again identified by PCR to ensure single organisms within the culture.

Table 2 summarizes number of bacterial strains isolated via serial dilution of feces from the single individual at risk for RA.

TABLE 2

| | Number of isolates |
|---|---|
| Lachno/Rumino amplification by PCR | 7 (14%) |
| No Lachno/Rumino amplification by PCR | 43 (86%) |
| Total | 50 |

As summarized in Table 2, a total of 50 isolates were established and seven were identified as Lachnospiraceae/Ruminococcaceae by qPCR (termed isolates 1-7). Five of the seven were confirmed as pure isolates by 16S rRNA sequencing (isolates 1, 3-5, and 7). The five isolates then underwent whole genome sequencing. The whole genome sequences were assembled, scaffolded, and cleaned using Abyss. The scaffolded sequences were input into the Biobakery Workflow and categorized as unidentified species within Ruminococcaceae *Subdoligranulum*, which the inventors designated as didolesgii.

Experimental Example 4 mAbs identified in Experimental Example 1 as having dual binding to synovial antigens and bacteria in the families Lachnospiraceae and Ruminococcaceae were mixed in excess with isolated strains identified as belonging to families Lachno/Rumino (0.5 μg IgG against $5\times10^{6}$ bacteria). The percentage of bacteria bound was then measured by flow cytometry. mAbs that did not bind bacteria were used as negative controls.

Figure 3A:
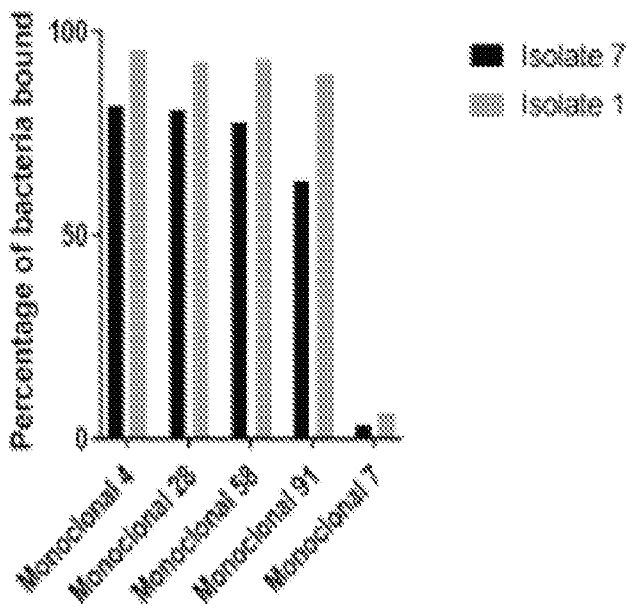
FIG. 3A is a bar chart illustrating the percentage of $5\times10^6$ bacteria of Isolate 1 (*Subdoligranulum didolesgii* strain H3) or Isolate 7 (*Subdoligranulum didolesgii* strain D8) bound by (0.5 microgram) representative mAbs from FIG. 1A.

FIG. 3A depicts the percentage of bacterial isolate bound (y-axis) by the mAb (x-axis) for two of the strains isolated from the single individual at risk for RA in Experimental Example 3: Isolate 1 (also referred to herein as Strain 1, Isolate H3, Strain H3, and *Subdoligranulum didolesgii* strain H3), and Isolate 7 (also referred to herein as Strain 7, Isolate D8, Strain D8, and *Subdoligranulum didolesgii* strain D8). Representative results using mAbs MH4, MH28, MH58, and MH91 are depicted. They were also matched against a control mAb (number 7) that was previously found to not bind bacteria.

Figure 3B:
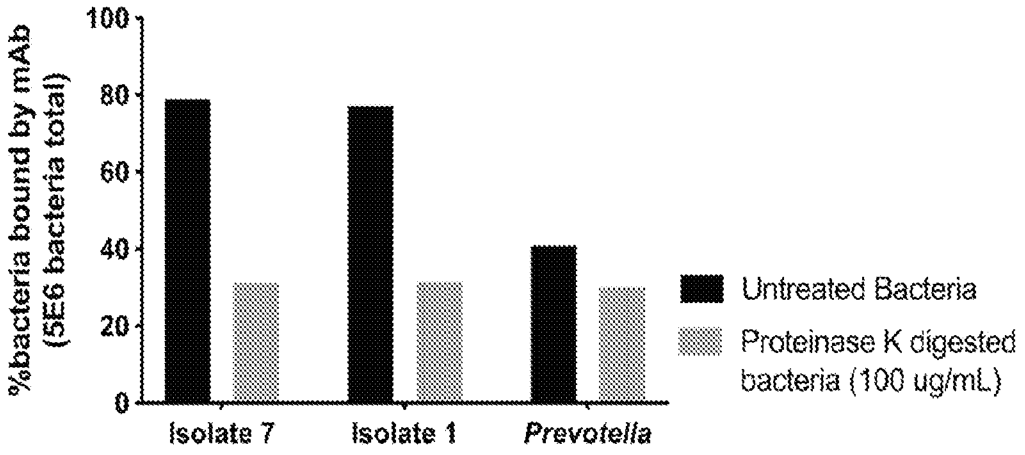
FIG. 3B is a bar chart illustrating the percentage of $5\times10^6$ bacteria of Isolate 7 (*Subdoligranulum didolesgii* strain D8), Isolate 1 (*Subdoligranulum didolesgii* strain H3), and a control bacteria (*Prevotella copri*) bound by representative mAb MH91, wherein bacteria are untreated or treated with proteinase K.

To test whether the mAbs target the bacteria in a protein-dependent manner, Isolates 1, 7, and *Prevotella copri* (control) were treated with 100 μg/ml proteinase K and washed prior to mixing with mAbs. The ability to then bind the bacteria was then measured by flow cytometry. FIG. 3B depicts representative results using mAb MH91, indicating the percent of total bacteria bound by the antibody for Isolates 1 and 7, and *Prevotella copri*, a bacterial species previously associated with RA. The data indicate that certain antibodies derived from circulating plasmablasts in individuals at risk for developing RA target isolated strains from families Lachno/Rumino in a protein-dependent manner.

Experimental Example 5

Serum from patients with RA or healthy controls (HC) was mixed with $5\times10^{6}$ of either Isolate 1 or Isolate 2 to determine whether patients with RA have elevated levels of antibodies to either isolate. Serum dilution was optimized by creating a dilution curve and was set at 1:60. Serum bound to bacteria was stained with anti-human IgG and anti-human IgA PE, as well as an anti-nucleic acid stain (Syto9 Green) to detect bacteria. Flow cytometric analysis were preformed to determine binding to the target bacterial strains.

Figure 4A:
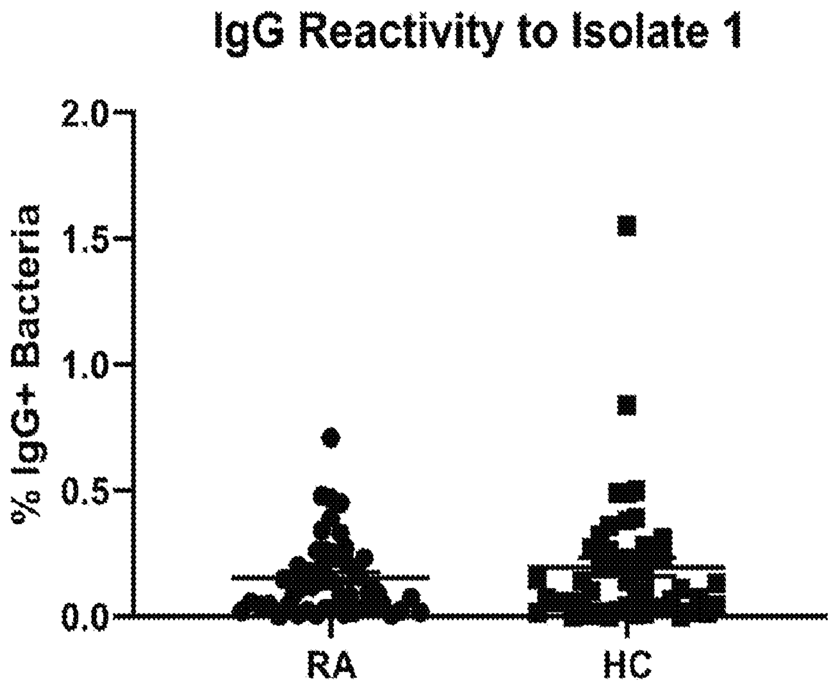
FIG. 4A is a dot plot illustrating the percent of bacteria of Isolate 1 (*Subdoligranulum didolesgii* strain H3) bound by serum IgG from patients with RA or healthy control (HC).
Figure 4B:
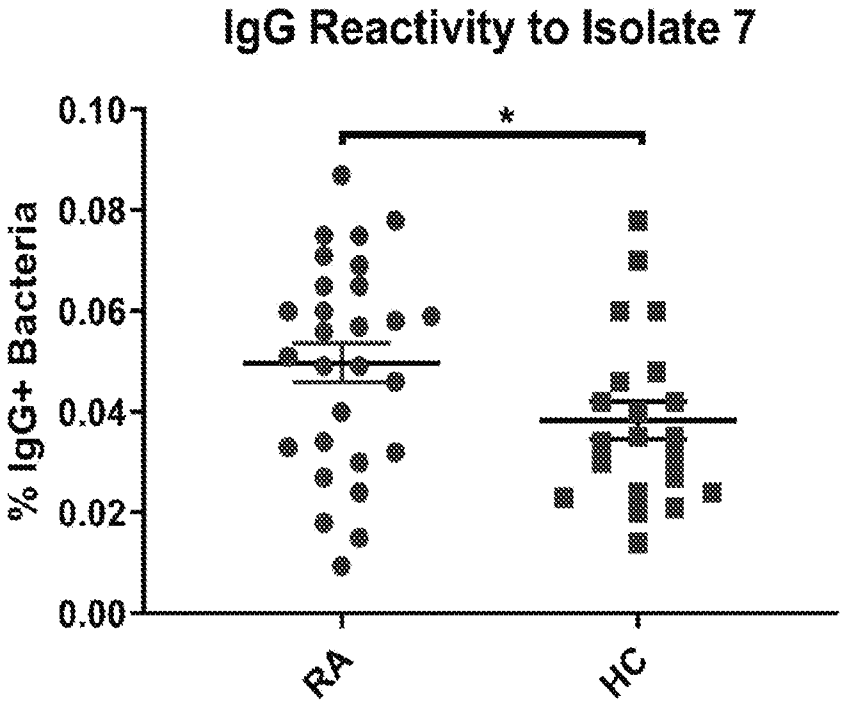
FIG. 4B is a dot plot illustrating the percent of bacteria of Isolate 7 (*Subdoligranulum didolesgii* strain D8) bound by serum IgG from patients with RA or healthy control (HC). *=P<0.05.

FIGS. 4A and 4B depict serum reactivity with Isolate 1 and Isolate 7, respectively. The percent of bacteria bound by serum IgG is shown for each individual, with the bars representing the mean±SEM for the group. *=P>0.05 by unpaired T-test. The results clearly indicate that serum from patients with RA have elevated levels of specific antibodies targeting Isolate 7, but not Isolate 1.

Figure 4C:
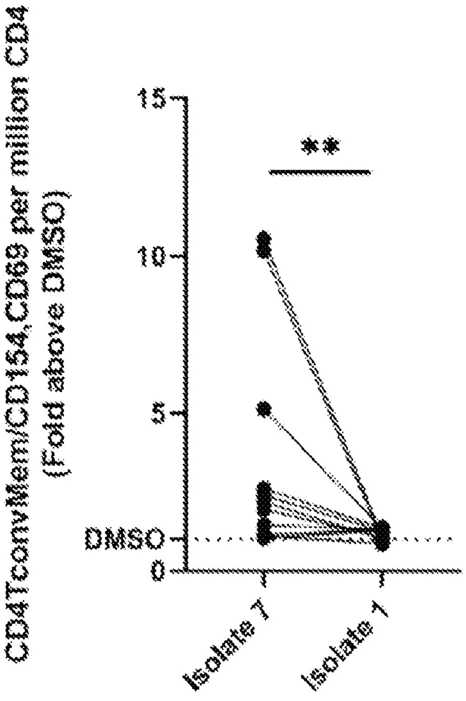
FIG. 4C depicts data from exposing Isolate 1 or 7 to isolated human peripheral blood mononuclear cells (PBMCs) from RA cases (n=11). PBMC were stimulated 14 hours in 37° C. incubator in the presence of either 0.1% DMSO, 50 ng/mL isolate 7 or 50 ng/mL isolate 1. **=P<0.01.
Figure 4D:
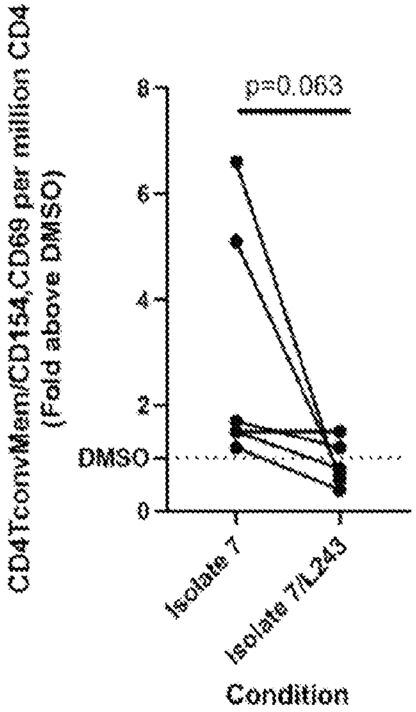
FIG. 4D depicts data from exposing Isolate 7 to isolated human peripheral blood mononuclear cells (PBMCs) from RA cases (n=11), rested in either anti-HLADR (clone L243) or anti-HLADQ (clone SVPL3) at 20 ug/mL, or equal volume PBS, 30 minutes prior to stimulation and Isolate 7.

To further support the immunologic relevance of the *Subdoligranulum* isolates, the inventors assessed if the bacteria were recognized by circulating T cells from individuals with RA. In brief, PBMCs from 11 individuals with RA were stimulated for 14 hours with 50 ng/ml oxygen-killed *Subdoligranulum* isolate 1 or isolate 7. Compared to isolate 1, isolate 7 significantly activated CD4+ T cells in the PBMCs as measured by surface CD69 and CD154 expression (FIG. 4C). T cell activation was MHC class II dependent, since blocking with anti-HLADR4 abrogated CD69 and CD154 expression (FIG. 4D).

Together, these findings support the hypothesis that the *Subdoligranulum* isolate 7 is immunologically relevant and strain variations may be of importance to understanding the pathogenesis of RA.

Experimental Example 6

In view of the results of Experimental Examples 4 and 5 involving Isolates 1 and 7, the inventors investigated whether either of these isolates on their own were capable of inducing arthritis. Male and female 6 to 8-week-old germ-free DBA/1 mice housed in sterile vinyl isolators were orally gavaged at day 0 with either sterile PBS, $10^{7}$ CFU *Prevotella copri*, a bacterial species previously associated with RA, $5\times10^{6}$ CFU Isolate 1, or $5\times10^{6}$ CFU Isolate 7.

Figure 5A:
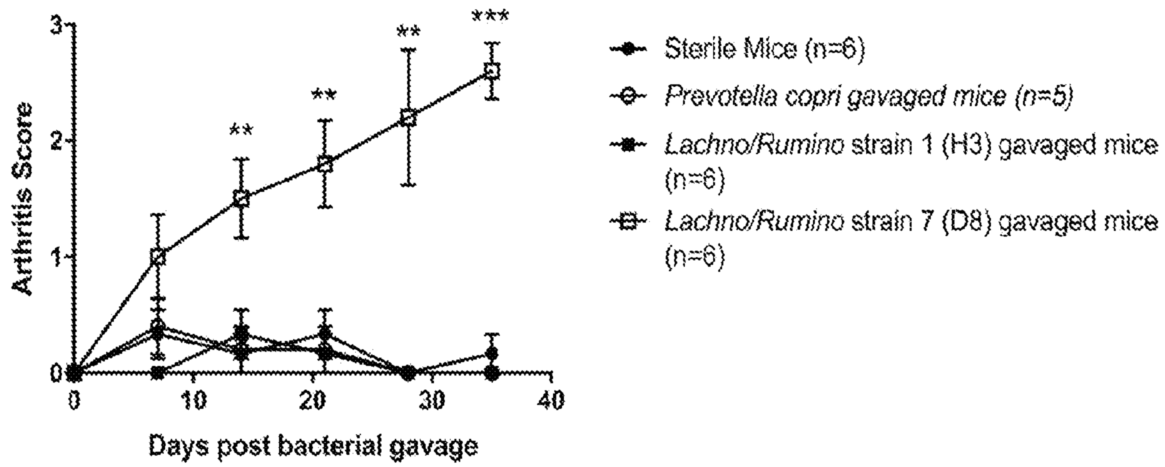
FIG. 5A is a line graph depicting arthritis scores for mice subjected to the indicated treatment over the course of 35 days. =P<0.01 and *=P<0.001.

Mice were scored by an observer blinded to the treatment group for signs of joint swelling and assessed a score of severity based on 0=now swelling, 1=1 digit swollen, 2=2 digits swollen, 3=3 digits swollen, and 4=entire paw swollen with ankylosis. The score for all four paws was summed for the animal's arthritis score. The results are summarized in FIG. 5A. Data are the mean arthritis scores in the indicated treatment group±SEM. Statistical significance was determined by unpaired t-tests (=P<0.01 and *=P<0.001).

Figure 5B:
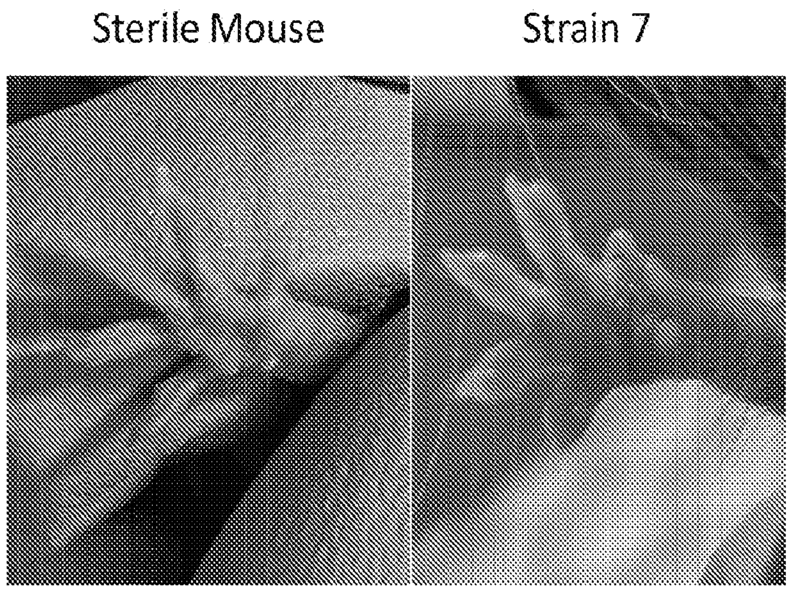
FIG. 5B presents two photographs of the forepaw of a mouse gavaged with sterile PBS ("Sterile mouse"; (left) and of a germ-free mouse mono-colonized with Isolate 7 (*Subdoligranulum didolesgii* strain D8) ("Strain 7"; right).

FIG. 5B depicts representative photographs of a forepaw of a mouse gavaged with sterile PBS (left) and that of a germ-free mouse mono-colonized with Isolate 7, in which swelling of digits and the wrist is clearly visible.

Figure 5C:
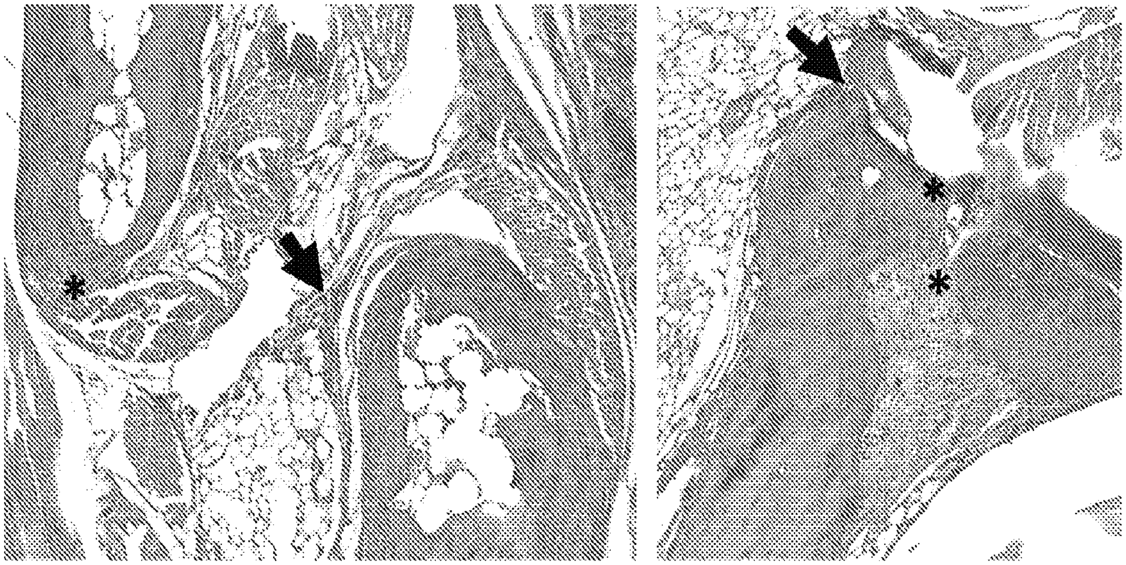
FIG. 5C presents two histological micrographs of mouse paws harvested 35 days following colonization with Isolate 7 (*Subdoligranulum didolesgii* strain D8). Images are displayed at 10× magnification.
Figure 5D:
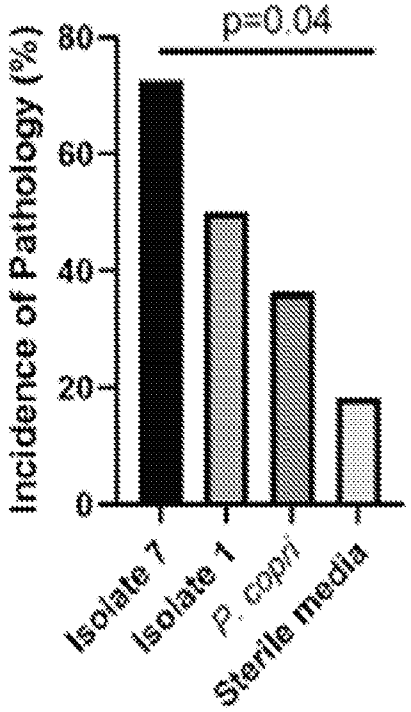
FIG. 5D is a graph showing incidence of pathology among all monocolonized mice. Fisher's exact test was performed, p=0.04.
Figure 5E:
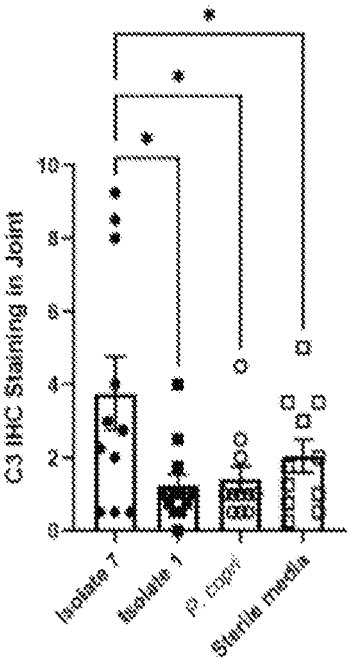
FIG. 5E is a graph of IHC data against the C3 component of the complement cascade. Scoring classification for C3 staining intensity for all mice is displayed. (n=12 isolate 1 gavaged, n=11 isolate 7 gavaged, n=11 *P. copri* gavaged, and n=11 sterile media gavaged, across two experiments).

35 days following colonization, mice were euthanized and paws harvested and stored in 10% formalin for histological analysis. The paws were decalcified with EDTA and sectioned. Hematoxylin and Eosin staining was performed and paw pathology was assessed by a pathologist in a blinded fashion. Evaluation of pathology demonstrated a range of synovitis, osteomyelitis, vasculitis, and soft tissue inflammation, all mild in severity. Representative sections from mice mono-colonized with Isolate 7 are depicted in the micrographs of FIG. 5C, demonstrating areas of synovial (arrows) and cartilage/bone destruction from inflammation (asterisks) due to Isolate 7. Micrographs are presented at 10× magnification. Mice colonized with isolate 7 had the highest incidence of pathology compared to the other treatment groups. See FIG. 5D. Immunohistochemistry (IHC) against the C3 component of the complement cascade was performed on the decalcified paw sections. The data demonstrated marked deposition both in the joint space and intradermally. See FIG. 5E.

In order to understand the systemic immune response following mono-colonization with isolate 1, isolate 7, or *P. copri*, or given sterile media, serum from mice was collected on days 14 and 35 after gavage. The total serum IgA was significantly increased in isolate 7 mono-colonized mice at day 14 as compared to the other groups (FIG. 5F), but this normalized by day 35 and was not observed for total serum IgG.

Figures 5F, 5G:
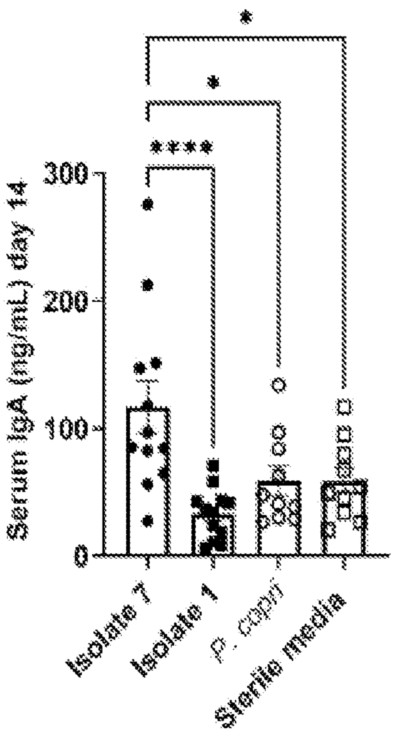
FIG. 5F is a graph of the total serum IgA at 14 days after gavage as determined by ELISA (n=12 isolate 7 gavaged, n=12 isolate 1 gavaged, n=10 *P. copri* gavaged, and n=10 sterile media gavaged).
FIG. 5G is a summary of the statistical test results for target autoantigens. Sera was analyzed on a planar array containing ~350 citrullinated and native peptides for autoantigens relevant in RA. An cutoff for reactivity was established and the proportion of murine samples meeting or exceeding this threshold for 11 target antigens at each timepoint is displayed.

The serum was evaluated for specific antibody reactivity through binding to a planar array containing ~350 RA-relevant autoantigenic targets. Interestingly, Isolate 7 gavaged mice developed and maintained serum autoantibodies against RA-relevant autoantigens at higher proportions at day 14 after bacterial gavage ($P<0.05$ by Kruskal-Wallis) than mice in the other treatment groups. Furthermore, isolate 7 mono-colonized mice developed numerous specific autoantibodies targeting RA-relevant antigens such as fibromodulin at greater titers in comparison to the control groups (FIG. 5G). These data indicate that mono-colonization with isolate 7 allows for the establishment of long-lived RA-relevant autoantibodies in circulation.

Figure 5H:
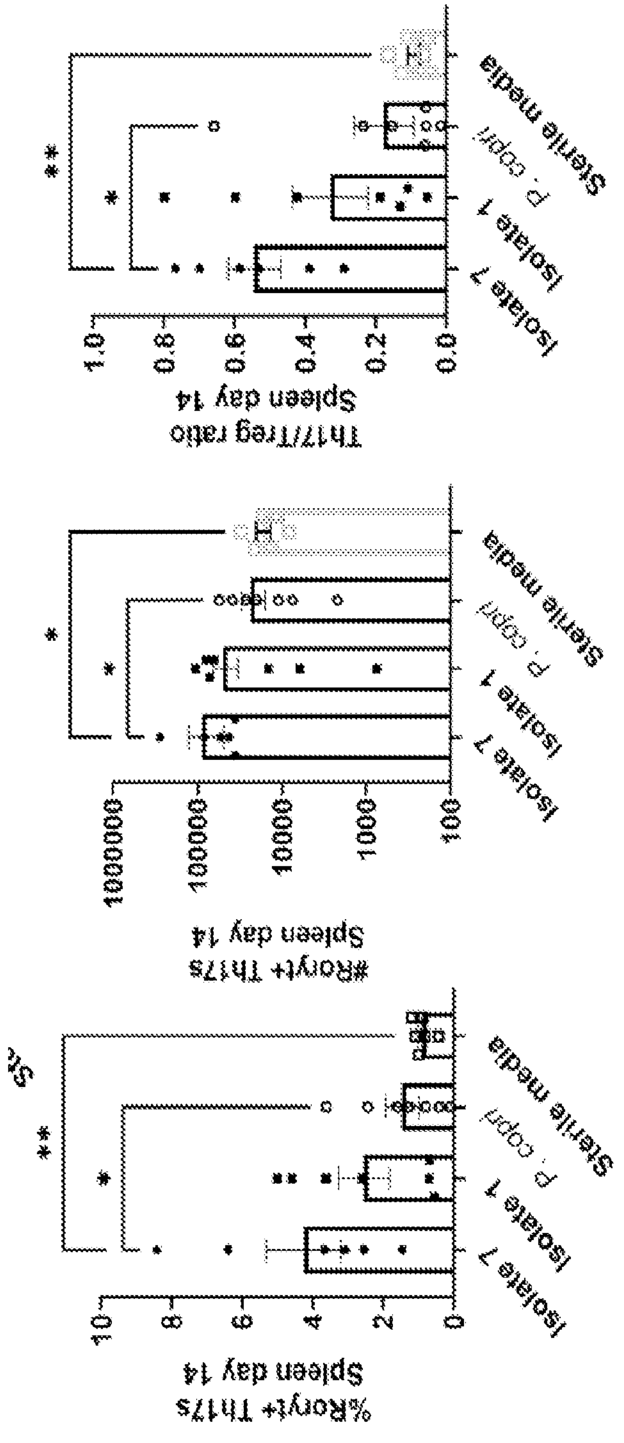
FIG. 5H depicts the percentage and absolute number of Rorγt+ Th17 cells as well as the Th17 to Treg ratio in spleens were collected from mice at 35 days post gavage. CD4+ T cell populations were analyzed by flow cytometry (n=7 isolate 7 gavaged, n=7 isolate 1 gavaged, n=6 *P. copri* gavaged, and n=8 sterile media gavaged).

Given the presence of CD4+ T cell reactivity to isolate 7 in patients with RA, splenic T cell populations were evaluated at days 14 and 35 in mice mono-colonized with isolate 1, isolate 7, or *P. copri*, or gavaged with sterile media. Th17 and Treg populations were focused on due to the role of intestinal microbiota in their development, and on Tfh because of the observed changes herein in autoantibodies. At day 14, splenic Th17 cells were significantly increased in percentage, absolute number, and Th17/Treg ratio in isolate 7 mono-colonized mice compared to *P. copri* and sterile media gavaged mice (FIG. 5H). However, significant differences in Treg or Tfh subsets was not observed. By day 35, the expansion of Th17 cells remained in isolate 7 mono-colonized mice compared to sterile media gavaged mice. These data are consistent with others' findings of Th17 expansion aiding in the development of autoantibody mediated arthritis in mice and in the evolution of human RA.

Because mono-colonization with Isolate 1 and 7 had such diverging effects, any similarities between the two isolates was examined. DNA was extracted from cultured Isolate 1 and Isolate 7. An Illumina NGS platform was employed, yielding short DNA sequences that were assembled into contigs and a genome scaffold using the Assembly By Short Sequences (ABySS) parallelized sequence assembler. Contigs were also filtered for and removed of any contaminant DNA. Strain identity was first established using Metagenomic Phylogenetic Analysis (MetaPhlAn 2.0) and was then confirmed through NCBI Blast of the scaffolded reads. The reference genome for family Ruminococcaceae genus *Subdoligranulum* used by MetaPhlAn 2.0 and to establish sequence identity was species 4_3_54A2FAA. Percent identity was determined by NCBI Blast, aligning each genomic scaffold with either the reference genome or other strain genome to get an overall percent homology.

Table 3 summarizes the percent identity of Isolates 1 and 7 relative to the reference OTU, as well as each other. Both Isolate 1 and Isolate 7 were determined to be novel strains of a novel species, and were named *Subdoligranulum didolesgii* strain H3 and *Subdoligranulum didolesgii* strain D8, respectively.

TABLE 3

| | OTU identification | Percent identity between isolate and reference OTU | Percent identity between Isolate 1 and Isolate 2 | Novel strain name |
|---|---|---|---|---|
| Isolate 1 | Family Ruminococcaceae, Genus *Subdoligranulum* unidentified species | 69.37% (80808/116485 bp) | 99.4% (2380873/2393298 bp) | *Subdoligranulum didolesgii* strain H3 |
| Isolate 7 | Family Ruminococcaceae, Genus *Subdoligranulum* unidentified species | 20.02% (25420/126994 bp) | | *Subdoligranulum didolesgii* strain D8 |

Figure 6:
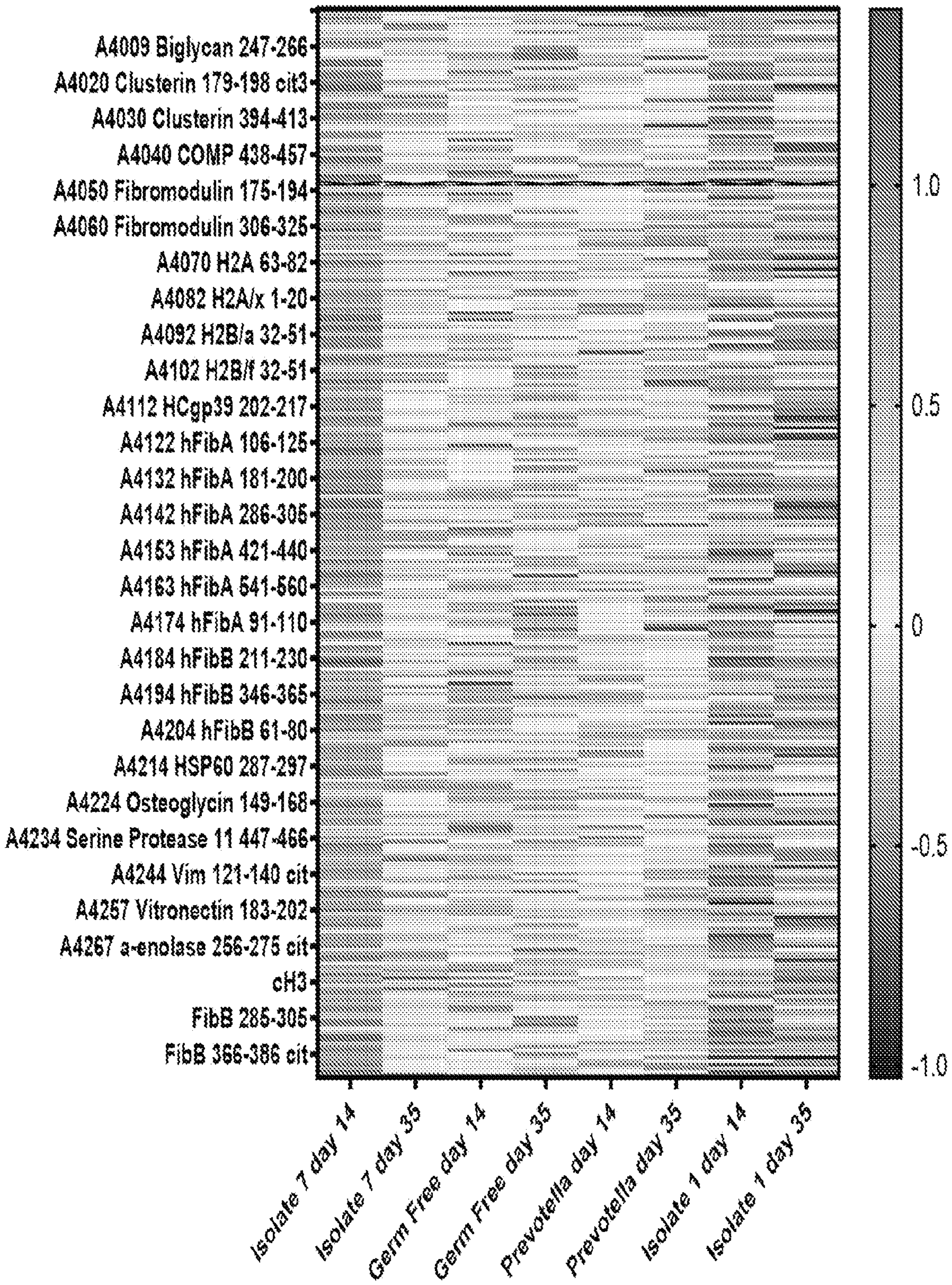
FIG. 6 is a heatmap representing binding of serum from germ-free DBA/1 mice gavaged with either sterile PBS, Isolate 1 (*Subdoligranulum didolesgii* strain H3), or Isolate 7 (*Subdoligranulum didolesgii* strain D8) with antigens of a murine synovial antigen protein array containing both citrullinated and non-citrullinated peptides and proteins.

Serum from germ-free DBA/1 mice mono-colonized with either sterile PBS (n=6) or $10^7$ CFU *Prevotella copri* (N=6), Isolate 1 (N-6), or Isolate 7 (n=6) were tested for antibodies targeting synovial antigens. Serum from days 14 and 35 from each group were applied to a murine synovial antigen protein array that contains both citrullinated and uncitrullinated peptides and proteins. FIG. 6 depicts a heatmap representing the z-score of relative reactivity from −1 (blue) to 1.5 (red) between serum (x-axis) and antigen (y-axis). Colonization with Isolate 7 caused the development of antibodies that bind synovial antigen, while Isolate 1 largely failed to do so.

Experimental Example 7

Figure 7A:
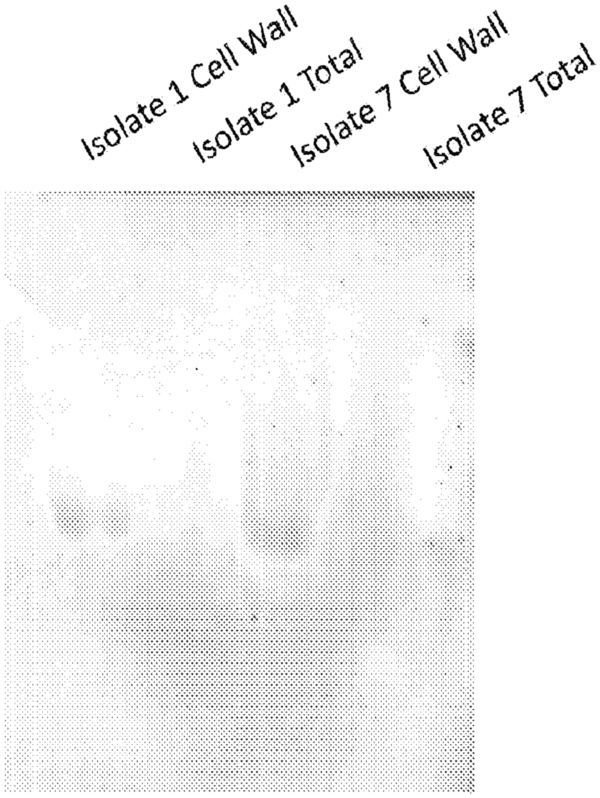
FIG. 7A is a photograph of a 10% native gel on which solubilized protein fractions (cell wall or total cell) from Isolate 1 (*Subdoligranulum didolesgii* strain H3) and Isolate 7 (*Subdoligranulum didolesgii* strain D8) were loaded and blotted against mAb MH91.

Protein fractionation was performed for Isolates 1 and 7 in which total protein was extracted using B-PER Protein Extraction reagent. The cell wall-specific protein fraction was isolated and solubilized through mutanolysin digest. The solubilized proteins were run on 10% native gels and were blotted against MH91, known to bind to the bacterial isolates. A representative native gel is depicted in the photograph of FIG. 7A.

Figure 7B:
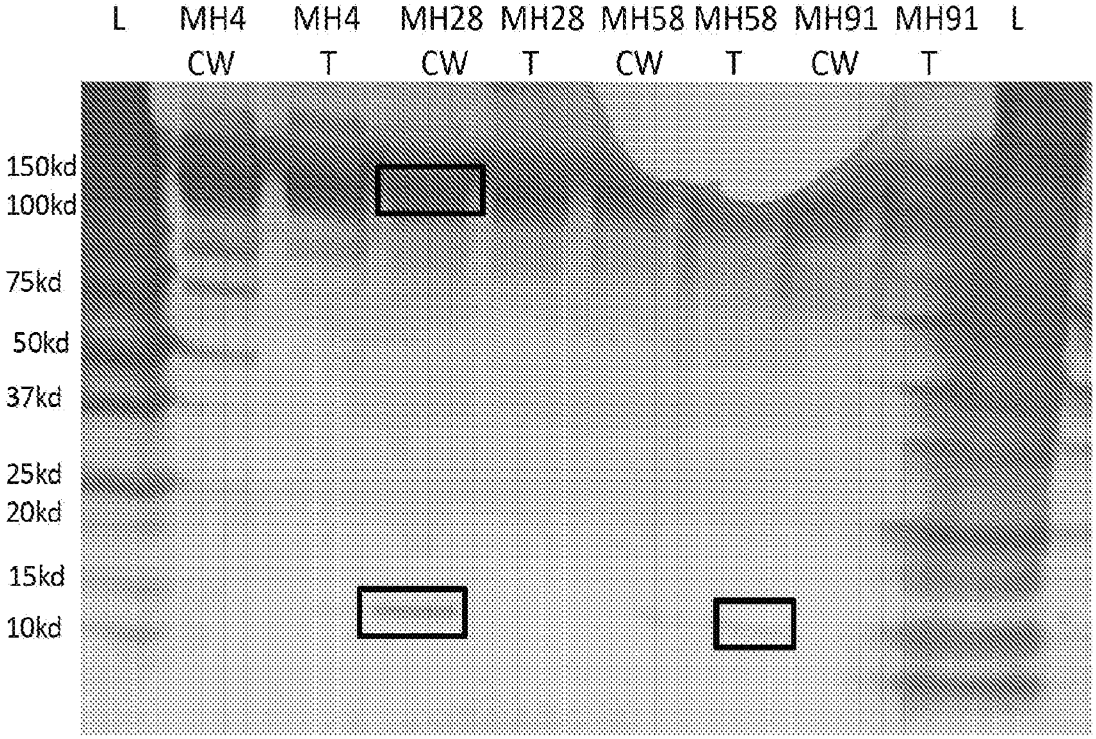
FIG. 7B is a photograph of a 10% SDS PAGE gel, depicting immunoprecipitation of proteins of Isolate 7 (*Subdoligranulum didolesgii* strain D8) using the indicated mAbs. CW=cell wall; T=total.

Four representative monoclonal antibodies identified in Experimental Examples 1 and 4 as capable of binding to Isolates 1 and 7 as well as synovial antigens (i.e., MH4, MH28, MH58, and MH91) were utilized to immunoprecipitate target proteins using the Invitrogen immunoprecipitation with Protein A protocol. These mAbs were exposed to the same two protein fractions described above, referring to FIG. 7A, and immunoprecipitated proteins were uncoupled from the antibodies and run on a 10% SDS PAGE gel prior to silver staining. FIG. 7B depicts a representative SDS PAGE gel.

The immunoprecipitated bands were excised and trypsin digested, and then MALDI-TOF was preformed to generate a list of component peptides. From here, protein identification from the component peptide library was performed using the MS-Homology tool available through Protein Prospector. Each peptide library was matched against 4 different databases to identify proteins of high likelihood across multiple databases. To verify these results utilizing a second method, each de novo peptide was run through a peptide BLAST search on NCBI to determine high-likelihood protein candidates. High-likelihood candidates were screened for evidence of protein generation by Ruminococcaceae species, and then the genome sequences were searched for evidence of the gene controlling each protein's production using the GeneWise Pairwise Sequence Alignment tool through EMBL-EMI. From these methods, several high-likelihood protein targets were identified. Protein targets are listed in Table 4.

TABLE 4

| Protein Name | Protein ID |
|---|---|
| Amino acid ABC transporter substrate-binding protein, PAAT family | R5Y4K6_9FIRM |
| Elongation factor Tu | R5YCH3_9FIRM |
| dTDP-glucose 4,6-dehydratase | R6DWD2_9FIRM |
| FG-GAP repeat domain-containing protein (plasmid) | A7B574_RUMGV |
| GTPases - translation elongation factors, partial | WP_009866873.1 |
| Putative DNA-binding protein | R5QFF1_9FIRM |
| Short-chain dehydrogenase/reductase SDR | D4M4P2_9FIRM |
| Transposase | R7CQ18_9FIRM |
| 3-phosphoshikimate 1-carboxyvinyltransferase | R6U1K9_9CLOT |
| ABC transporter, substrate-binding protein, family 5 domain protein | A0A171JU57 |
| MFS transporter | R5YDJ5_9FIRM |
| IgG-binding protein A | 586027 M |
| 4-hydroxybenzoate octaprenyltransferase | Q3SLJ4 |

Experimental Example 8

Cecal contents from germ-free DBA/1 mice mono-colonized with sterile PBS or $10^7$ CFU *Prevotella copri*, Isolate 1, or Isolate 7 were evaluated for >190 metabolites using LC-MS.

Figure 8A:
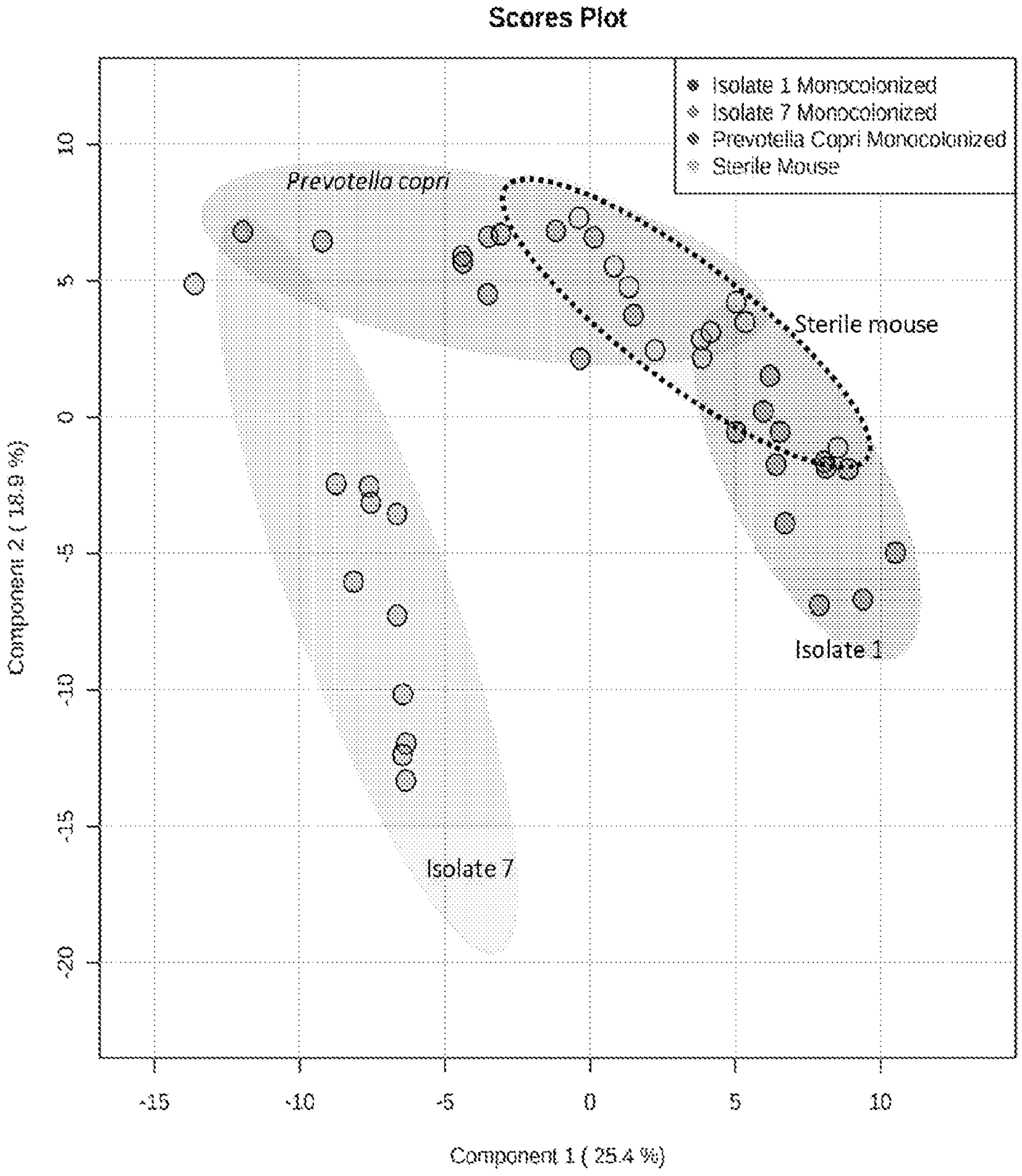
FIG. 8A is a principle components analysis plot depicting metabolic profiles for Isolate 1 (*Subdoligranulum didolesgii* strain H3), Isolate 7 (*Subdoligranulum didolesgii* strain D8), and *Prevotella copri* mono-colonized mice, and sterile mice.

The data presented in FIG. 8A provide a comparison of the treatment groups, and demonstrate separation of metabolic profiles between Isolate 7 (green) and the control groups (isolate 1=red, *P. copri*=blue, and sterile mice=cyan).

Figure 8B:
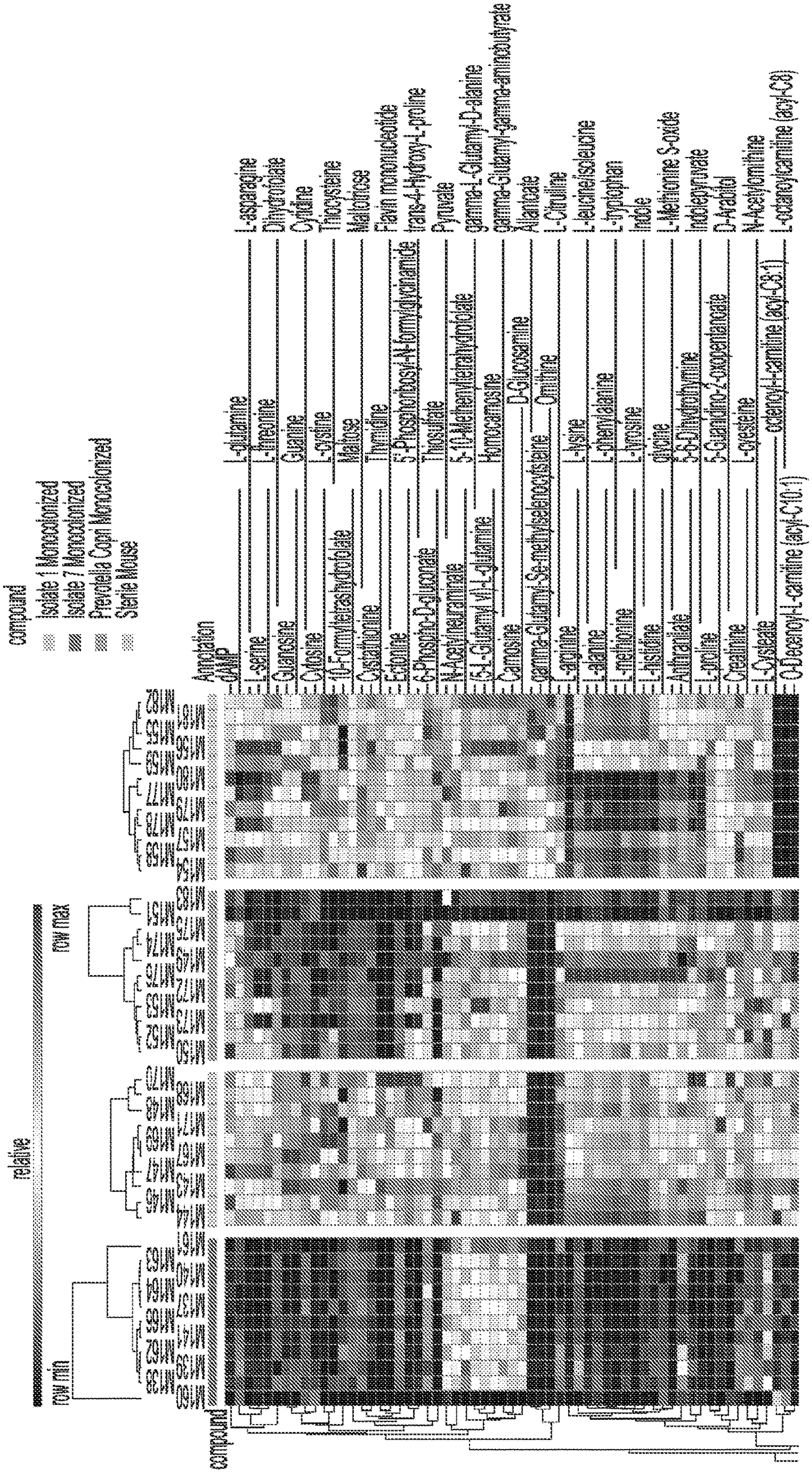
FIG. 8B is a heatmap representing relative metabolite abundance, where columns are individual mice grouped by treatment, and rows are specific metabolites.
Figure 8B:
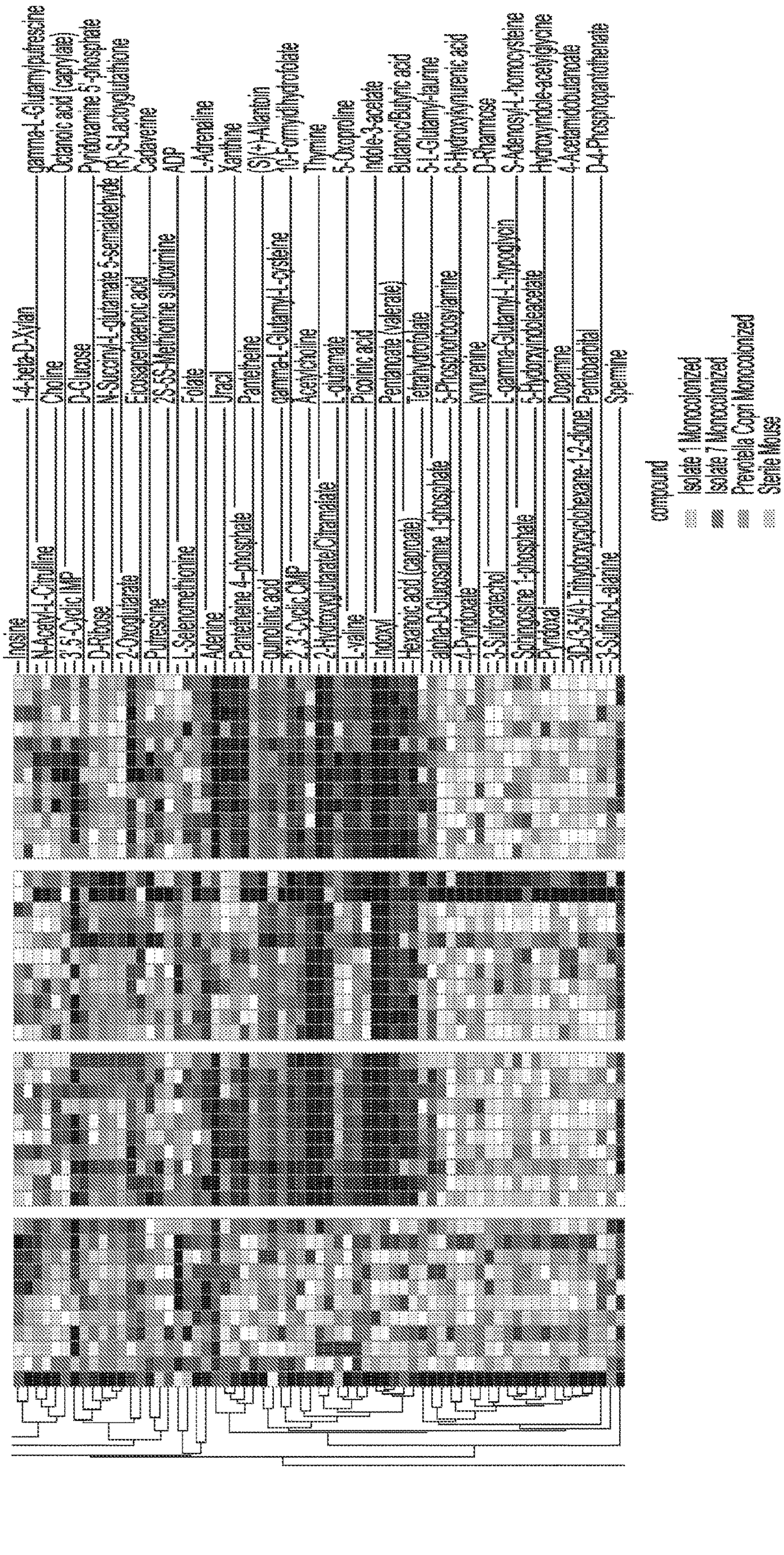
Figure 8B:
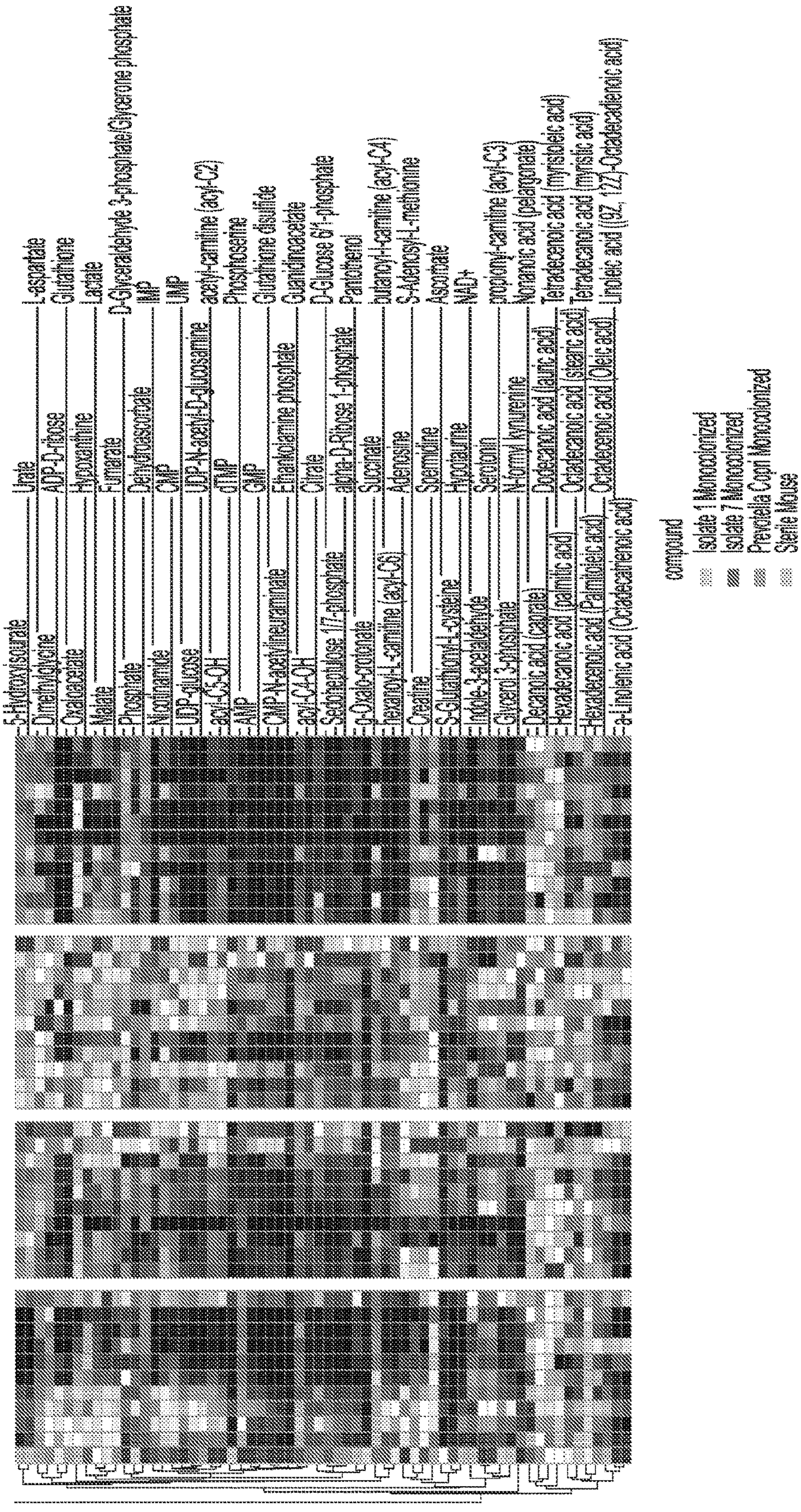

FIG. 8B depicts a heatmap representing relative metabolite abundance from low (blue) to high (red). Columns are individual mice grouped by treatment and rows are specific metabolites. As depicted, the mice mono-colonized with Isolate 7 develop a unique cecal metabolome, characterized by increased indole derivatives.

Figure 8C:
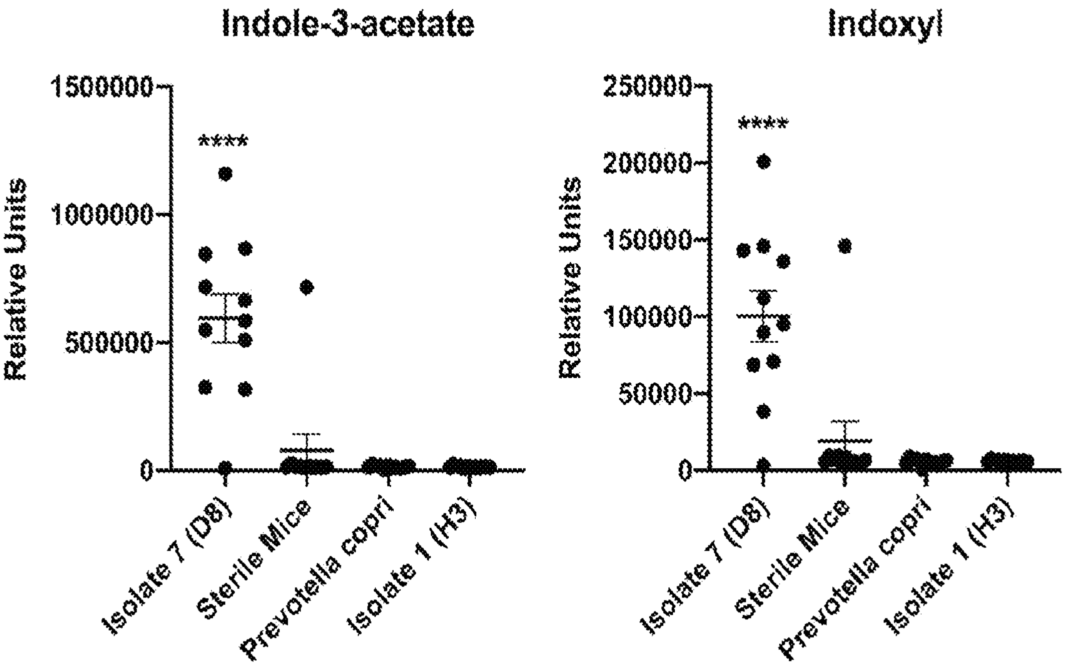
FIG. 8C is a dot plot illustrating relative units of metabolites in the tryptophan-indole pathway (indole-3-acetate), and indoxyl. ****=P<0.0001.

As indicated by the data summarized in FIG. 8C, two bacteria-specific metabolites in the tryptophan-indole pathway—indole-3-acetate and indoxyl—were significantly elevated in the ceca of germ free mice mono-colonized with isolate 7 compared to the other 3 groups. The relative value of each metabolite for each mouse is shown, with bars as mean±SEM (****=P<0.0001 by ANOVA).

Experimental Example 9

Figure 9A:
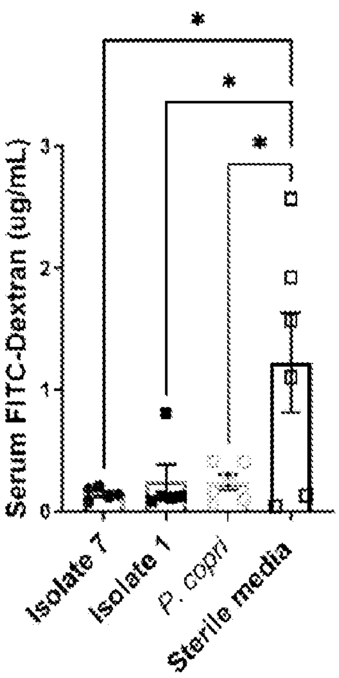
FIGS. 9A-9D (MS 5A) depict data indicated that *Subdoligranulum* strain 7 causes development of isolated lymphoid follicles in gut characterized by increased mucosal IgA and Th17 skewing in mucosal lymphoid tissues.
Figure 9B:
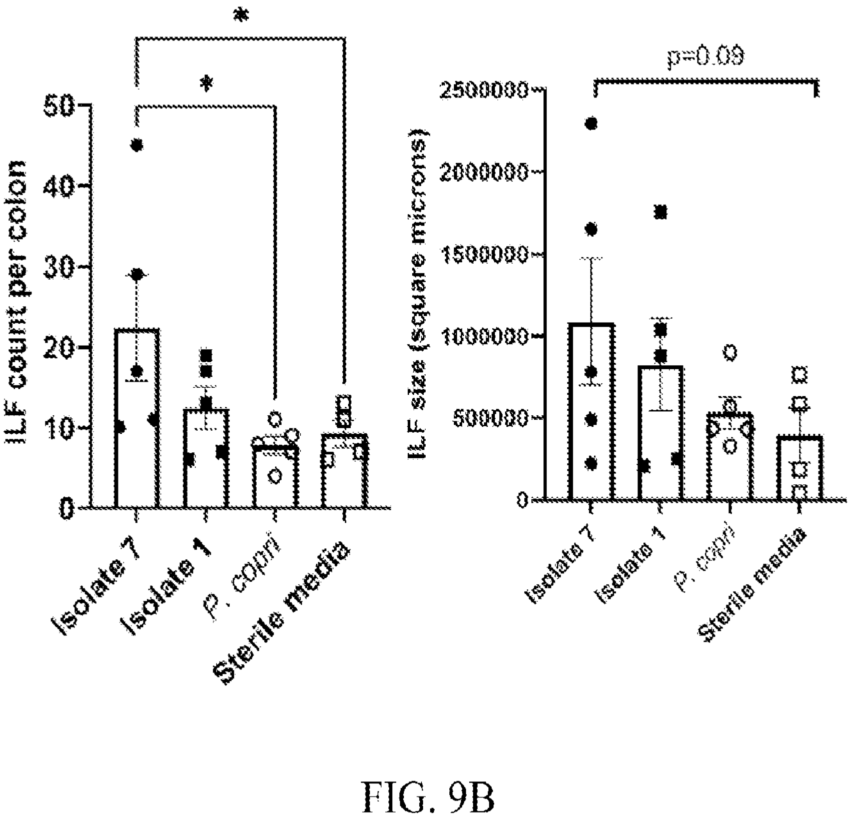
Figure 9C:
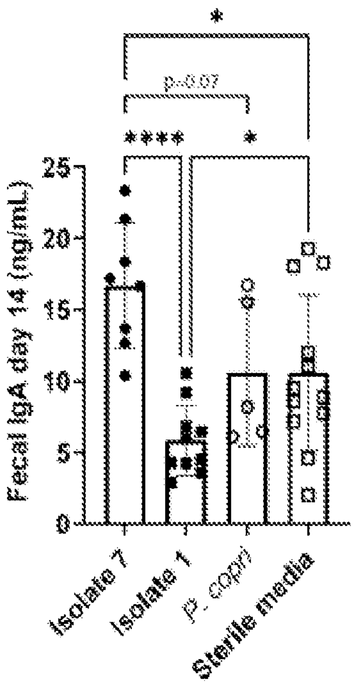
Figure 9D:
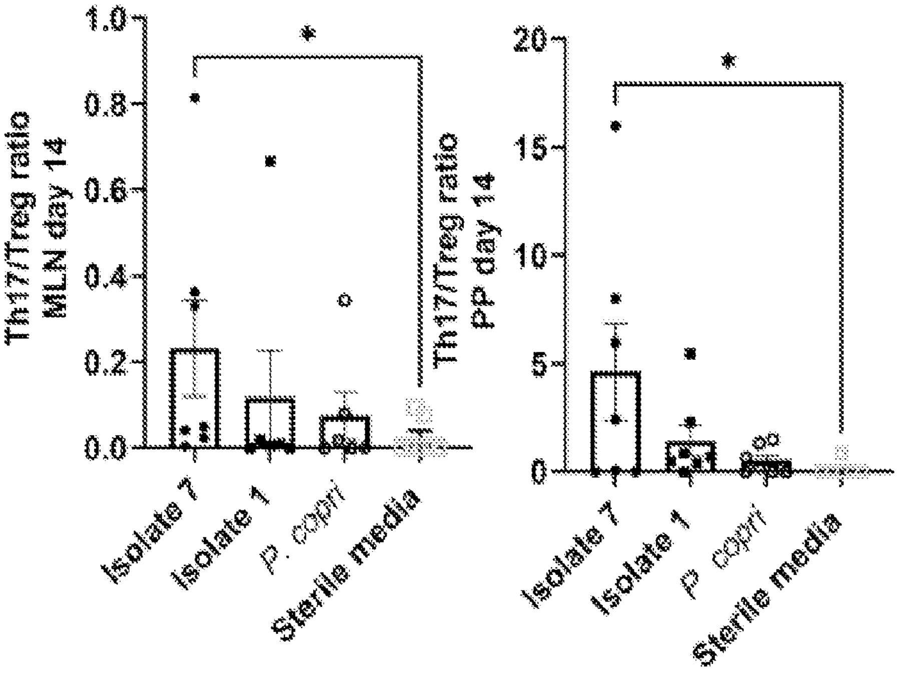

The effects of *Subdoligranulum* isolate 7 on intestinal mucosal immunity was investigated as follows. To determine if isolate 7 relative to isolate 1, *P. copri*, or sterile media affected intestinal permeability, FITC-dextran was administered orally to mice four hours prior to euthanasia, at which time sera was collected and the levels of FITC-dextran measured. All three mono-colonizations resulted in improved barrier compared to sterile media gavaged mice (FIG. 9A), indicating that the two *Subdoligranulum* isolates, as well as *P. copri*, were capable of at least partially restoring the barrier defect of germ free mice. Examination of the intestinal histology of mice from the four treatment groups revealed an increased number and of isolated lymphoid follicles (ILFs) in isolate 7 colonized mice as compared to *P. copri* and isolate 1 colonized mice, and a trend towards increased ILF size in isolate 7 gavaged mice (p=0.09 compared to sterile media gavaged mice) (FIG. 9B), without change of colonic crypt depth or small intestinal villus morphology among isolate 7 gavaged mice. Interestingly, there is an increase in villus width and crypt depth among isolate 1 gavaged mice which could suggest an mild injurious intestinal effect among mice gavaged with this strain. The ILFs in isolate 7 colonized mice were larger and more numerous as compared with other groups, and more closely resembled classical mature ILF morphology (FIG. 9B), suggesting increased mucosal IgA generation. Indeed, luminal IgA secretion was significantly increased in isolate 7 colonized mice as compared to the other treatment groups (FIG. 9C), although similar to the serum, this difference resolved by day 35. There was no significant difference in fecal IgG among groups. In associated mucosal lymphoid tissues mesenteric lymph nodes (MLNs) and Peyer's patches (PPs), the ratio of Th17/Treg T cell subsets increased significantly in the isolate 7 mono-colonized mice compared to sterile media gavaged mice at day 14 following gavage (FIG. 9D), although the percentages and absolute numbers were not significantly different. Collectively, these observations suggest that *Subdoligranulum* isolate 7 stimulates a robust intestinal immune response characterized by the formation of ILFs functioning to secrete IgA.

Experimental Example 10

Figure 10A:
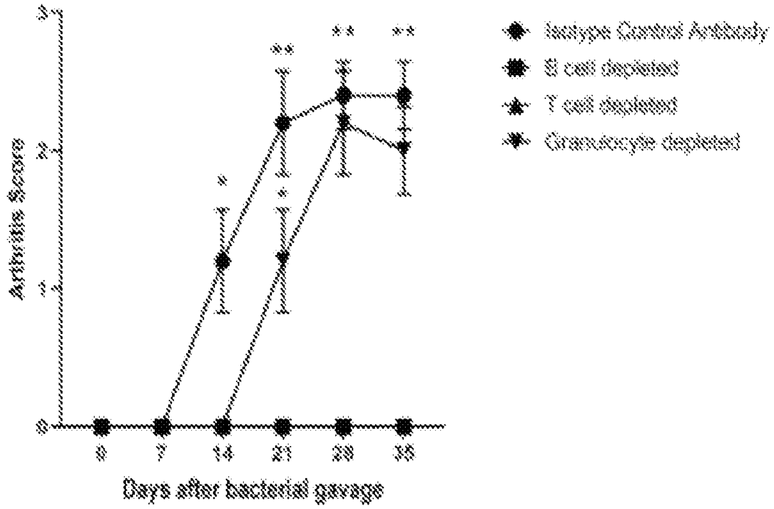
FIG. 10A-10G depict data from mice selectively deleted of their B cell, CD4+ T cell, or Neutrophil compartments (through IP administration of a depleting antibody) and monocolonized with isolate 7 forty-eight (48) hours after depletion of the targeted cell compartment.
Figure 10B:
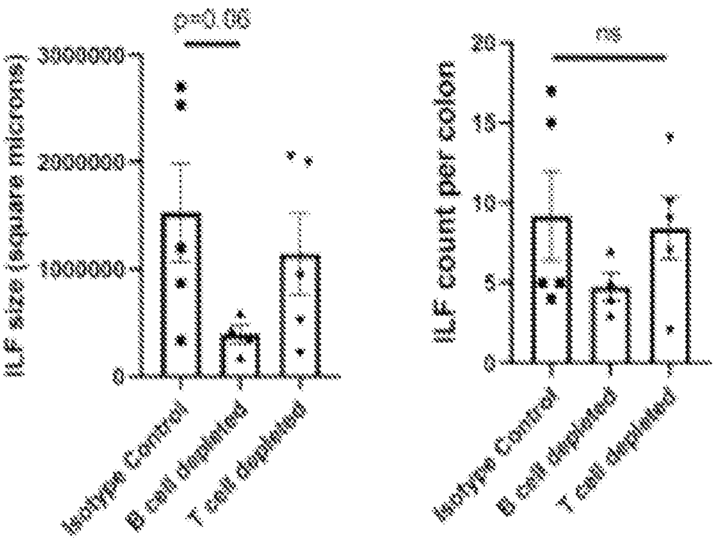
Figure 10C:
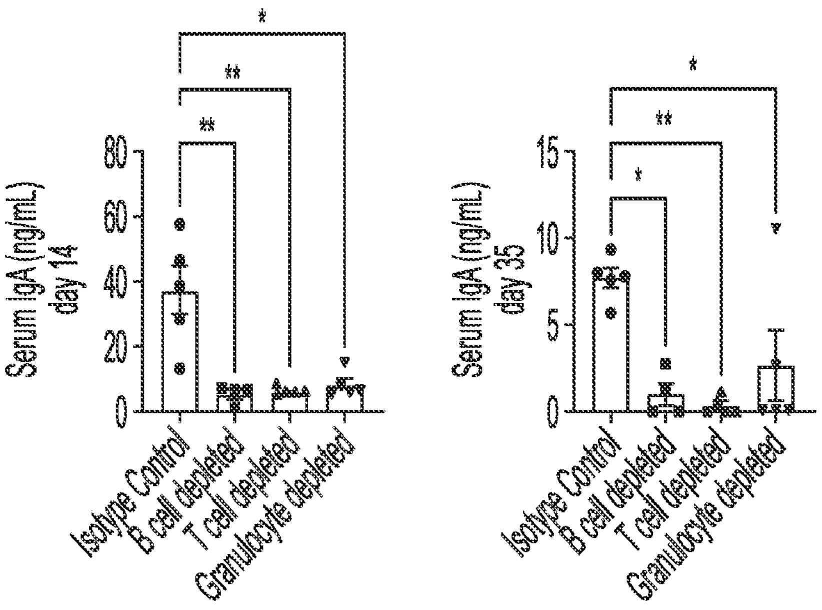
Figure 10D:
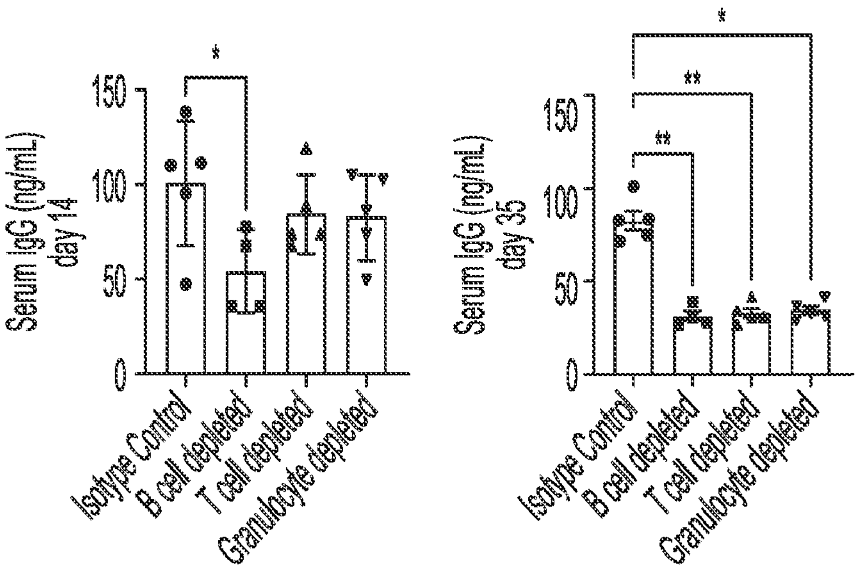
Figure 10E:
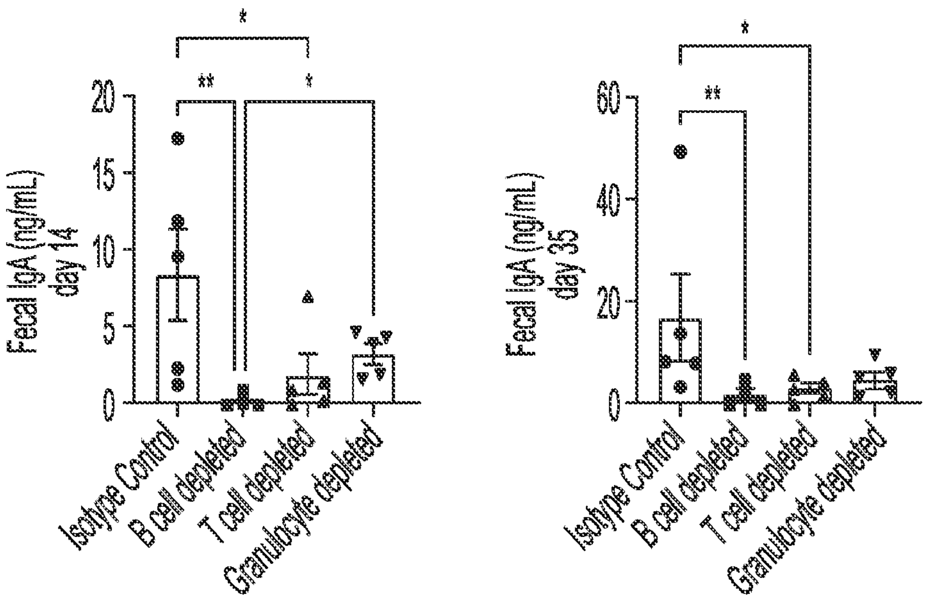
Figure 10F:
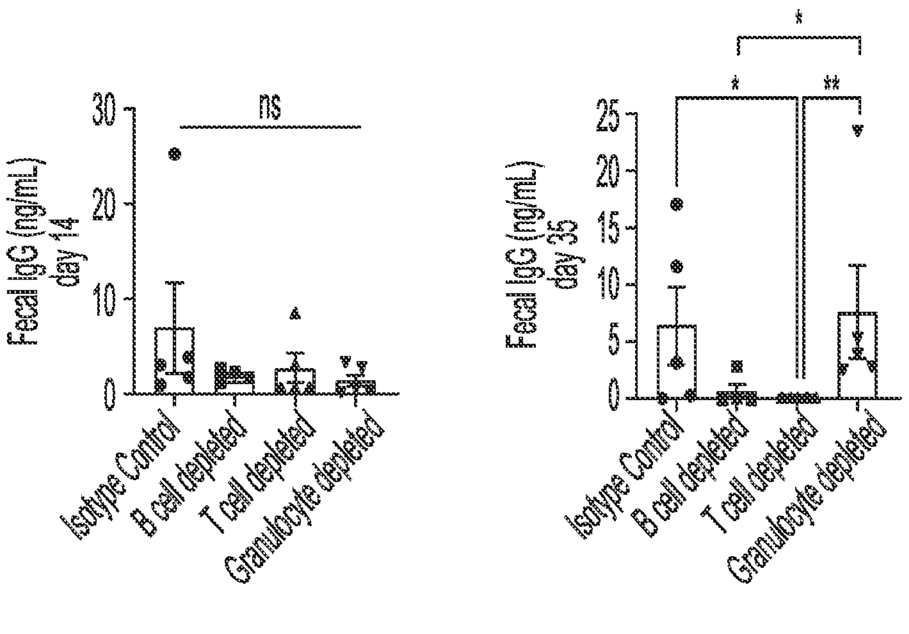

Joint Swelling in *Subdoligranulum* Isolate 7 Colonized Mice is Dependent on T and B Cells but not Granulocytes To determine if the observed paw swelling was truly mediated by adaptive immunity, B cells, T cells, or granulocytes were selectively depleted by using depleting mAbs two days prior to mono-colonizing mice with isolate 7. The mice that were depleted of T or B cells did not develop swelling, while control antibody treated mice did (FIG. 10A), indicating that adaptive immunity is required for the development of paw swelling. Though mice depleted of granulocytes developed paw swelling equal to treatment with control antibody, the onset of swelling was delayed by about one week (FIG. 10A), suggesting that while granulocytes aid in the phenotype, they are not essential. ILFs were not reduced in size or number in the T cell depleted mice, though they are reduced in size in the B cell depleted mice (p=0.06, FIG. 10B). In addition to reduced paw swelling and intestinal ILF formation, circulating and fecal IgA was decreased in the B and T cell depleted mice at days 14 and 35 after bacterial gavage, and circulating and fecal IgG was decreased at day 35 after bacterial gavage (FIG. 10C-10F). These data suggest a T cell dependent antibody response that occurs in response to this bacterial gavage. Interestingly, circulating IgG and IgA is also depleted in the granulocyte depleted mice, suggesting that granulocyte-dependent Ig synthesis at the mucosal surface that then spreads systemically may be important in this model of disease.

Figure 10G:
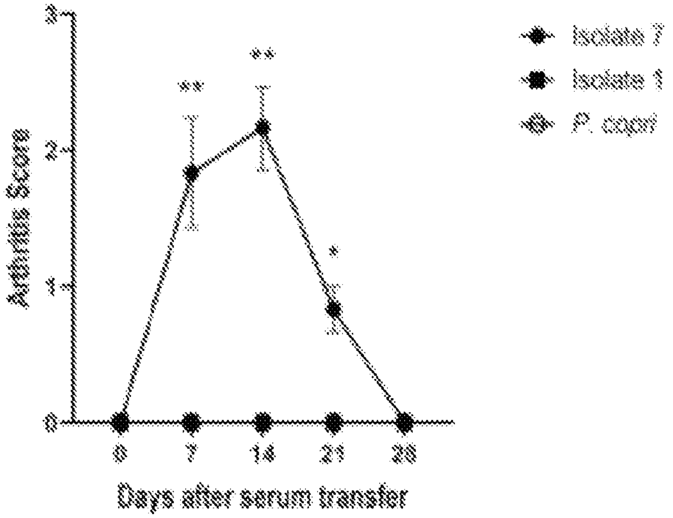

Since the isolate 7 colonized mice develop serum autoantibodies to RA-relevant antigens, the serum antibodies were assayed to determine if they were pathogenic. Serum was collected from mice 35 days after colonization with isolate 1, isolate 7, or *P. copri* mono-colonized mice and pooled by colonization group. Intraperitoneal injection of serum from isolate 7-colonized mice into healthy germ-free DBA/1 mice resulted in paw swelling observed within days and, similar to other serum transfer studies, resolves by 28 days following transfer, whereas sera from isolate 1 and *P. copri* colonized mice were unable to stimulate this phenotype (FIG. 10G). Taken together, these findings support a potential mechanism for *Subdoligranulum* isolate 7 inciting B cell autoimmunity through a local intestinal to systemic immune response.

SEQUENCE LISTING

The patent contains a lengthy sequence listing. A copy of the sequence listing is available in electronic form from the USPTO web site (https://seqdata.uspto.gov/docdetail?docId=US12800583B2). An electronic copy of the sequence listing will also be available from the USPTO upon request and payment of the fee set forth in 37 CFR 1.19(b)(3).

The invention claimed is:

1. A composition comprising at least one immunotherapeutic agent, wherein the at least one immunotherapeutic agent is an antibody, or an antigen-binding fragment thereof, against an antigen of *Subdoligranulum didolesgii* strain D8 wherein the antibody or antigen-binding fragment thereof comprises the variable heavy chain (VH) region and the variable light chain (VL) region of an antibody selected from the group consisting of:

MH4 ($V_H$=SEQ ID NO: 9; $V_L$=SEQ ID NO: 10);

MH28 ($V_H$=SEQ ID NO: 57; $V_L$=SEQ ID NO: 58);

MH58 ($V_H$=SEQ ID NO: 117; $V_L$=SEQ ID NO: 118); and

MH91 ($V_H$=SEQ ID NO: 183; $V_L$=SEQ ID NO: 184).

2. The composition of claim 1, further comprising an antibiotic effective against *Subdoligranulum didolesgii* strain D8.

3. A method for preparing a sample fraction for detection of *Subdoligranulum didolesgii* strain D8 in a subject, comprising contacting a sample from the subject selected from a fecal sample, a fecal swab, or an intestinal biopsy with an antibody or antigen-binding fragment thereof comprising the variable heavy chain (VH) region and the variable light chain (VL) region of an antibody selected from the group consisting of:

MH4 ($V_H$=SEQ ID NO: 9; $V_L$=SEQ ID NO: 10);

MH28 ($V_H$=SEQ ID NO: 57; $V_L$=SEQ ID NO: 58);

MH58 ($V_H$=SEQ ID NO: 117; $V_L$=SEQ ID NO: 118); and

MH91 ($V_H$=SEQ ID NO: 183; $V_L$=SEQ ID NO: 184); wherein after the contacting of the sample, the resulting fraction comprises an increased relative abundance of bacteria from Lachnospiraceae, Ruminococcaceae, or both Lachnospiraceae and Ruminococcaceae in the sample fraction.

* * * * *